(12) United States Patent
Takahashi et al.

(10) Patent No.: US 11,096,702 B2
(45) Date of Patent: Aug. 24, 2021

(54) REENTRY CATHETER

(71) Applicant: Asahi Intecc Co., Ltd., Seto (JP)

(72) Inventors: Katsunori Takahashi, Irvine, CA (US); Muneya Furukawa, Irvine, CA (US)

(73) Assignee: ASAHI INTECC CO., LTD., Seto (JP)

( * ) Notice: Subject to any disclaimer, the term of this patent is extended or adjusted under 35 U.S.C. 154(b) by 224 days.

(21) Appl. No.: 16/392,169

(22) Filed: Apr. 23, 2019

(65) Prior Publication Data
US 2019/0321059 A1 Oct. 24, 2019

Related U.S. Application Data

(60) Provisional application No. 62/662,042, filed on Apr. 24, 2018.

(51) Int. Cl.
*A61B 17/22* (2006.01)
*A61M 25/00* (2006.01)
*A61M 25/01* (2006.01)

(52) U.S. Cl.
CPC ........... *A61B 17/22* (2013.01); *A61M 25/007* (2013.01); *A61M 25/008* (2013.01);
(Continued)

(58) Field of Classification Search
CPC .... A61B 2017/22094; A61M 25/0068; A61M 2025/0108; A61M 25/0194;
(Continued)

(56) References Cited

U.S. PATENT DOCUMENTS

| | | | | |
|---|---|---|---|---|
| 4,583,968 A | * | 4/1986 | Mahurkar | A61M 5/1582 604/43 |
| 4,682,978 A | * | 7/1987 | Martin | A61M 5/1582 604/43 |

(Continued)

FOREIGN PATENT DOCUMENTS

| | | |
|---|---|---|
| JP | H06-319745 | 11/1994 |
| JP | 2004-350901 | 12/2004 |

OTHER PUBLICATIONS

International Search Report and Written Opinion dated Jun. 9, 2019 in the International Application No. PCT/US2019/028672.
(Continued)

*Primary Examiner* — Tan-Uyen T Ho
*Assistant Examiner* — Arwa Mostafa
(74) *Attorney, Agent, or Firm* — Oliff PLC

(57) ABSTRACT

A reentry catheter having a catheter body having a lumen extending axially through a length of the catheter body, a distal port in communication with the lumen, and a flexible distal tip positioned at a distal end of the catheter body. The distal tip can have a first planar surface and a second planar surface that are angled to form a tapered portion in the distal tip. A thickness of the tapered portion in a first direction can decrease along the length of the tapered portion and can be less than a width of the tapered portion in a second direction at every point along the length of the tapered portion such that the tapered portion of the tip is more flexible when bent in the first direction than in the second direction, the second direction being normal to the first direction.

23 Claims, 15 Drawing Sheets

(52) U.S. Cl.
CPC .... *A61M 25/0052* (2013.01); *A61M 25/0108* (2013.01); *A61B 2017/22038* (2013.01); *A61B 2017/22095* (2013.01)

(58) Field of Classification Search
CPC ...... A61M 25/0052; A61M 2025/0197; A61M 25/0102; A61M 25/0015; A61M 25/0012; A61M 25/00; A61M 25/001
See application file for complete search history.

(56) References Cited

U.S. PATENT DOCUMENTS

| | | | |
|---|---|---|---|
| 6,719,725 | B2 | 4/2004 | Milo et al. |
| 8,202,246 | B2 | 6/2012 | Kugler et al. |
| 8,636,715 | B2 | 1/2014 | Patel |
| 9,610,422 | B2 * | 4/2017 | Moehle ............. A61M 25/0068 |
| 2009/0264826 | A1 | 10/2009 | Thompson |
| 2012/0095485 | A1 * | 4/2012 | Cully ................ A61M 25/0054 606/159 |
| 2013/0012924 | A1 * | 1/2013 | Davis ..................... A61L 29/06 604/525 |
| 2013/0317528 | A1 | 11/2013 | Anderson et al. |
| 2014/0074108 | A1 | 3/2014 | Warren |
| 2014/0094741 | A1 * | 4/2014 | Bellisario ......... A61M 25/0071 604/39 |
| 2014/0194913 | A1 | 7/2014 | O'Day |
| 2015/0126972 | A1 | 5/2015 | Ravenscroft |
| 2016/0192952 | A1 | 7/2016 | Warren |
| 2016/0271374 | A1 | 9/2016 | Spencer |
| 2016/0302807 | A1 | 10/2016 | Anderson |
| 2016/0361076 | A1 | 12/2016 | Zhou et al. |
| 2017/0079671 | A1 | 3/2017 | Morero et al. |
| 2018/0093074 | A1 * | 4/2018 | Burkholz .......... A61M 25/0068 |

OTHER PUBLICATIONS

OUTBACK™ LTD™ Re-entry Catheter; True Lumen Re-entry Technology in 4 pages.
NAVICROSS® Support Catheter brochure in 8 pages.

\* cited by examiner

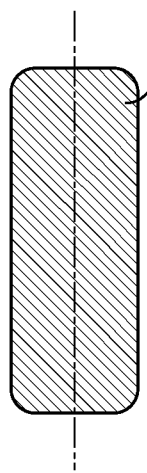 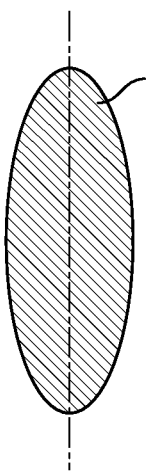 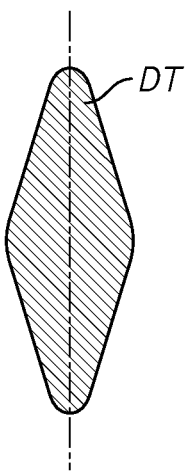 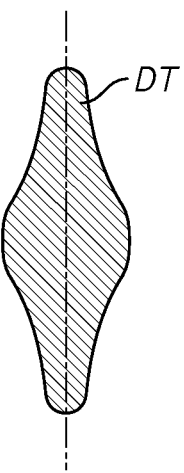
FIG. 22A        FIG. 22B        FIG. 22C        FIG. 22D
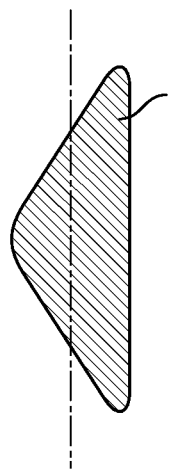 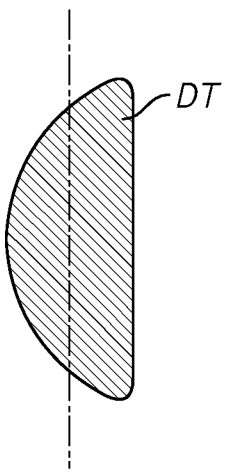
FIG. 22E        FIG. 22F
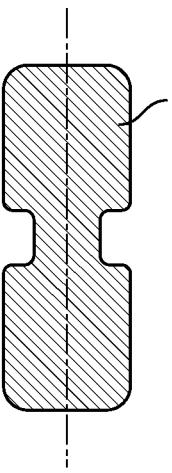 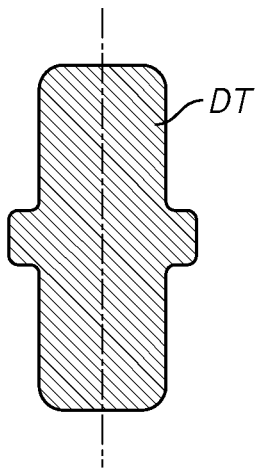
FIG. 22G        FIG. 22H

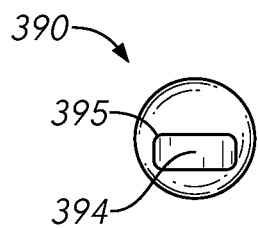
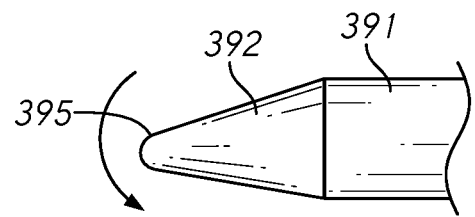
FIG. 28A  FIG. 28B
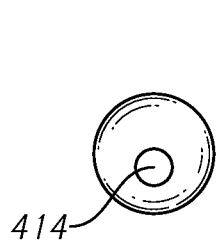
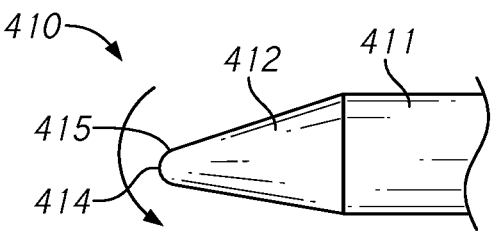
FIG. 29A  FIG. 29B
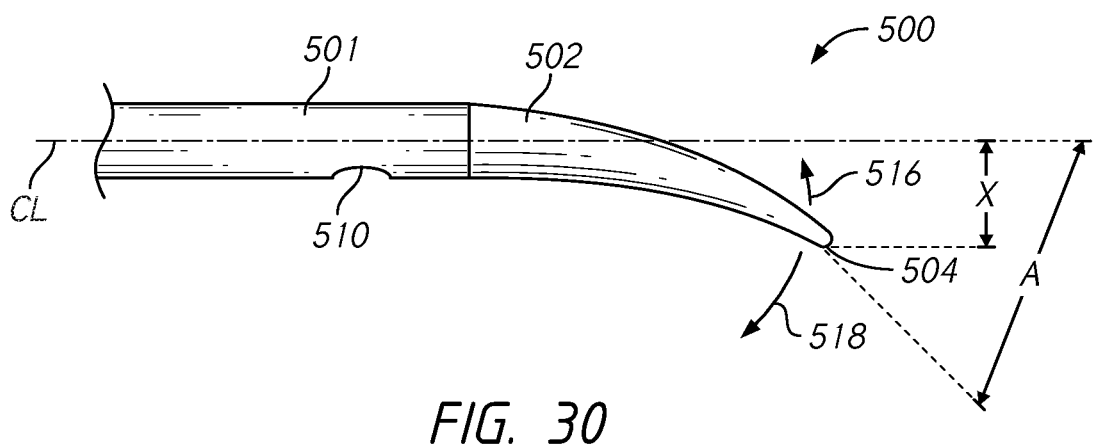
FIG. 30
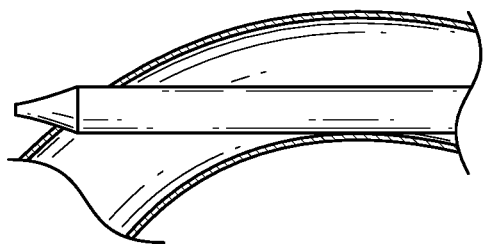
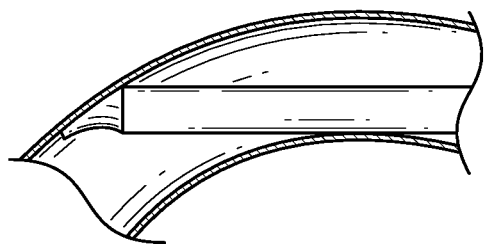
FIG. 31A  FIG. 31B

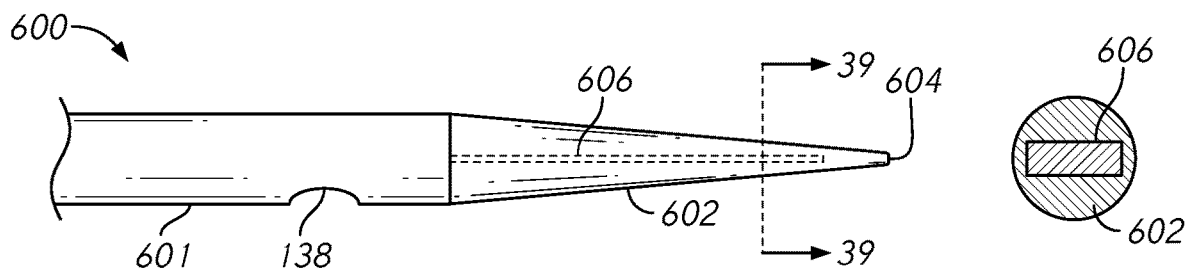
FIG. 38   FIG. 39
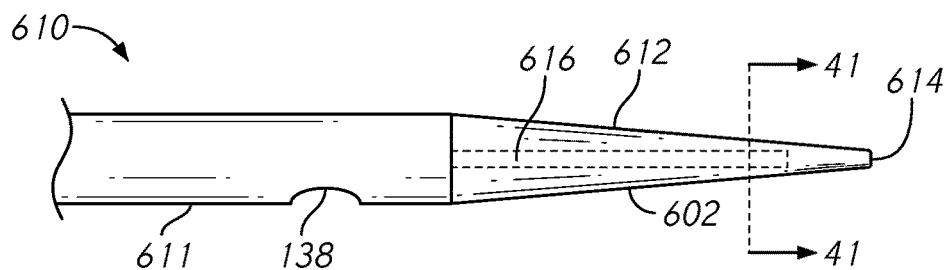
FIG. 40
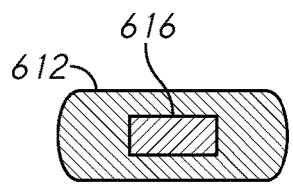   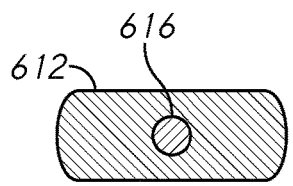
FIG. 41   FIG. 42
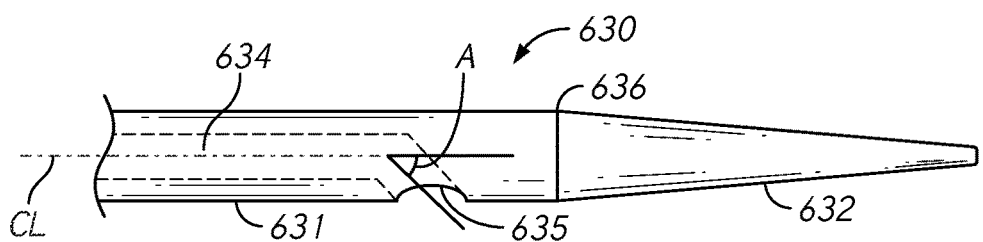
FIG. 43
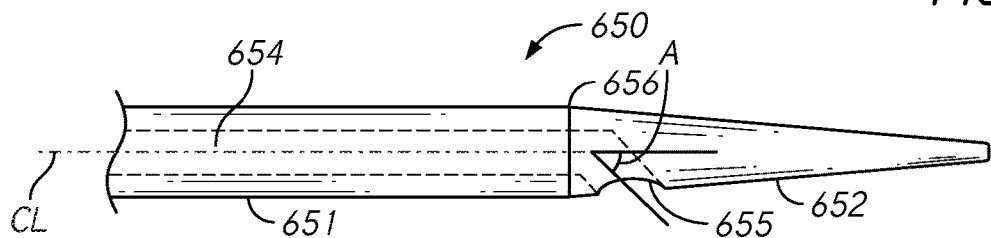
FIG. 44

REENTRY CATHETER

PRIORITY CLAIM AND INCORPORATION BY REFERENCE

The present application claims priority from U.S. Patent Application No. 62/662,042, filed on Apr. 24, 2018, titled REENTRY CATHETER AND METHOD OF USING SAME, the content of which is incorporated by reference herein in its entirety. The benefit of priority is claimed under the appropriate legal basis including, without limitation, under 35 U.S.C. § 119(e).

BACKGROUND OF THE DISCLOSURE

Field of the Disclosure

The disclosure relates to reentry catheters, in particular, to reentry catheters used for treatment of occluded vessels.

Background and Description of the Related Art

A chronic total occlusion (CTO) is a complete or substantially complete blockage in an artery that has been present for more than three months. These blockages can result from severe build-up of fatty deposits, plaque and/or calcium within the arteries (atherosclerosis) and are one of the complications from coronary artery disease (CAD). CAD occurs when the artery or arteries that supply blood to the heart become narrowed or blocked because of atherosclerosis. When the heart does not receive enough blood, a person may have chest pain (angina), shortness of breath or a heart attack. These symptoms occur with exertion and sometimes at rest. CTOs substantially or completely impede the flow of blood to the heart and can have severe effects on a patient's health. When one or more of a patient's coronary arteries are completely blocked, the patient will be at higher risk for a heart attack.

In the past, physicians relied on coronary artery bypass grafting, or open-heart surgery, as the main option for treating these blockages, in which a vein or artery from another part of the body is used to create a new route to the coronary artery that bypasses the blockage. Coronary artery bypass grafting was a highly invasive and risky procedure. Other techniques, including stenting, and atherectomy (plaque or obstruction is cut and removed from the artery), have been developed to treat CTOs.

Even the current treatment techniques and devices for CTO, however, are difficult, time-consuming, and present significant risks to the patient. Many current CTO treatment procedures require or involve the surgeon advancing a guidewire past the occlusion by advancing the guidewire through a subintimal portion of the vessel wall. The subintimal portion of an artery is situated between the intima (the innermost membrane or lining of a blood vessel) and the media of an artery wall. This typically involves penetrating the intima of a vessel wall on the proximal side of the blockage, advancing the guidewire through the subintimal portion of the artery wall past the blockage, and then re-entering the artery lumen by advancing the guidewire back through the intimal layer into the lumen.

Thereafter, with the guidewire in place, having bypassed the occlusion through the subintimal vessel wall portion, subsequent procedures can be performed. These include the procedures mentioned above, such as without limitation, angioplasty, stenting, etc. In procedures involving the introduction of a guidewire to the diseased portion of the artery, the manipulation of the guidewire itself makes the CTO procedure very difficult for even the most skilled surgeons. Crossing a CTO with a guidewire (i.e., advancing a guidewire past a CTO) in surgery can require many hours. Risks associated with the guidewire procedures include vessel perforation, vessel re-routing, long procedure time, inadvertent reentry (penetration from sub-intimal space to intimal space) in an undesired location, and other complications and risks.

Embodiments of the improved devices and methods disclosed herein provide lower risk, safer solutions for advancing a guidewire past an occlusion.

SUMMARY OF SOME EMBODIMENTS

The systems, methods and devices described herein have innovative aspects, no single one of which is indispensable or solely responsible for their desirable attributes. Without limiting the scope of the claims, some of the advantageous features will now be summarized.

Some embodiments disclosed herein are directed to a catheter (for example, but without limitation, a reentry catheter) having a catheter body having a first end and a second end, a lumen extending through a length of the catheter body, a distal port in communication with the lumen, and a distal tip positioned at a distal end of the catheter body. Any embodiments of the catheters disclosed herein can be used for reentry procedures. In any embodiments, the distal tip can be tapered along a length of the distal tip or otherwise configured such that a distal portion of the distal tip is more flexible (i.e., can flex, bend, or deflect with less applied force) than a proximal portion (i.e., the portion of distal tip closer to the catheter body) of the distal tip. Additionally, in any embodiments, the distal tip can have a greater thickness or greater stiffness (i.e., resistance to bending under an applied load or force) in a widthwise direction than a thickness or stiffness in a height or vertical direction so that the distal tip is more flexible in the height direction than in the widthwise direction. The distal port can be, but is not required to be, formed at an acute angle relative to an axial centerline of the catheter body. The catheter body can further have a radiopaque marker adjacent to the distal port.

Any of the embodiments disclosed herein can have any or any combination of any of the components, features, or details of any of the following arrangements.

Arrangement 1: A reentry catheter having a catheter body having a lumen extending axially through a length of the catheter body, a distal port in communication with the lumen, and a flexible distal tip positioned at a distal end of the catheter body. The distal tip can have a first planar surface and a second planar surface that are angled to form a tapered portion in the distal tip. A thickness of the tapered portion in a first direction can decrease along the length of the tapered portion and can be less than a width of the tapered portion in a second direction at every point along the length of the tapered portion such that the tapered portion of the tip is more flexible when bent in the first direction than in the second direction, the second direction being normal to the first direction.

In any arrangements or embodiments, including without limitation Arrangement 1, the first and second planar surfaces of the distal tip can extend along a length of the tapered portion generally to a distal end of the distal tip such that the tapered portion of the distal tip extends to the distal end of the distal tip. Additionally, a port can be formed in the catheter body so as to be in communication with the lumen and to direct a guidewire that is advanced through the lumen out of the port in a lateral direction, the lateral direction being in a plane that is coincident with the first direction of the tapered portion and intersects the axial centerline of the catheter body. The distal port can be at an acute angle relative to an axial centerline of the catheter body.

Arrangement 2: The reentry catheter of Arrangement 1, wherein the tapered portion can be at least approximately two times as flexible in the first direction as compared to the second direction at every point along the length of the tapered portion.

Arrangement 3: The reentry catheter of any of the previous Arrangements, wherein the tapered portion can be from approximately three times to approximately five times as flexible in the first direction as compared to the second direction at every point along the length of the tapered portion.

Arrangement 4: The reentry catheter of any of the previous Arrangements, wherein the distal tip can have an asymmetric shape such that the distal tip can be more flexible in the first direction than in a third direction, wherein the third direction is opposite to the first direction.

Arrangement 5: The reentry catheter of any of the previous Arrangements, wherein the distal end portion of the distal tip can be offset from a centerline of the distal tip by a distance that can be from approximately 10% to approximately 50% of the diameter of the catheter body.

Arrangement 6: The reentry catheter of any of the previous Arrangements, wherein, at any point along the tapered portion of the distal tip, a second moment of area of the distal tip in the second direction can be greater than a second moment of area of the distal tip in the first direction.

Arrangement 7: The reentry catheter of any of the previous Arrangements, wherein a second moment of area of the distal tip in the second direction can be greater than a second moment of area of the distal tip in the first direction at all points along a length of the tapered portion and wherein a difference between the second moment of area of the distal tip in the second direction and the second moment of area of the distal tip in the first direction increases along the length of the tapered portion.

Arrangement 8: The reentry catheter of any of the previous Arrangements, wherein a second moment of area of the distal tip in the second direction can be at least approximately 20 times greater than a second moment of area of the distal tip in the first direction at the distal end of the tapered portion.

Arrangement 9: The reentry catheter of any of the previous Arrangements, further comprising a radiopaque marker adjacent to the distal port.

Arrangement 10: The reentry catheter of any of the previous Arrangements, further comprising a core member positioned in the tapered portion configured to increase a bending stiffness of the distal tip in the second direction more than in the first direction.

Arrangement 11: The reentry catheter of any of the previous Arrangements, wherein the port can be configured to direct a guidewire that is advanced through the lumen out of the port at an angle of from approximately 35 degrees to approximately 90 degrees relative to the axial centerline of the catheter body.

Arrangement 12: The reentry catheter of any of the previous Arrangements, wherein a distal edge of the distal tip can have a rounded distal edge.

Arrangement 13: The reentry catheter of any of the previous Arrangements, wherein the tapered portion of the distal tip can have a first and a second side surface that are generally flat along the length of the tapered portion.

Arrangement 14: The reentry catheter of any of the previous Arrangements, wherein the width of the tapered portion of the distal tip can linearly decrease along the length of the tapered portion.

Arrangement 15: The reentry catheter of any of the previous Arrangements, wherein the tapered portion of the distal tip can have a first and a second side surface that are generally curved along the length of the tapered portion so that a width of the tapered portion can be nonlinearly decreasing.

Arrangement 16: The reentry catheter of any of the previous Arrangements, wherein the tapered portion of the distal tip can have a first and a second side surface that are generally curved in the first direction so that the first and second side surfaces have a curved shape in a cross section of the tapered portion.

Arrangement 17: The reentry catheter of any of the previous Arrangements, wherein the first and second planar surfaces can have a length from approximately 0.020 in (0.5 mm) to approximately 0.79 in (20 mm) and wherein the distal end of the distal tip has a thickness greater than or equal to approximately 0.002 in (0.05 mm) and less than a diameter of the catheter body.

Arrangement 18: The reentry catheter of any of the previous Arrangements, wherein the catheter body can have one or more of single wire braiding, multi-wire braiding, coils, and any other suitable metal support structures.

Arrangement 19: The reentry catheter of any of the previous Arrangements, wherein the catheter body can have one or more of single wire braiding, multi-wire braiding, coils, and any other suitable metal support structures made from stainless steel, tungsten, Co—Cr, or Ni—Ti.

Arrangement 20: The reentry catheter of any of the previous Arrangements, wherein a diameter of the catheter body can be from approximately 2 Fr to approximately 6 Fr.

Arrangement 21: A reentry catheter having a catheter body having a first end and a second end, a lumen extending axially through a length of the catheter body, a distal port in communication with the lumen, the distal port extending generally in a first direction away from an axial centerline of the catheter body, and a flexible distal tip positioned at a distal end of the catheter body, a distal end portion of the distal tip having. The distal tip can have a first stiffness when a distal end portion of the distal tip is bent in the first direction and a second stiffness when the distal end portion of the distal tip is bent in a second direction that is normal to the first direction. In any embodiments disclosed herein, the second stiffness of the distal tip when the distal tip is bent in the second direction is greater (which can be substantially greater) than the first stiffness of the distal tip when the distal tip is bent in the first direction at every point along a length of the distal tip. Furthermore, the first stiffness of the distal tip when the distal end portion of the distal tip is bent in the first direction can decrease along the length of the distal tip such that the first stiffness is lowest at the distal end of the distal tip.

Arrangement 22: The reentry catheter of Arrangement 21, wherein the second stiffness of the distal end portion of the distal tip when the distal end portion of the distal tip is bent in the second direction is at least approximately twice as high as the first stiffness of the distal end portion of the distal tip when the distal end portion of the distal tip is bent in the first direction.

Arrangement 23: The reentry catheter of any one of Arrangements 21-22, wherein the second stiffness of the distal end portion of the distal tip when the distal end portion of the distal tip is bent in the second direction is at least approximately three times as high as the first stiffness of the distal end portion of the distal tip when the distal end portion of the distal tip is bent in the first direction.

Arrangement 24: The reentry catheter of any one of Arrangements 21-23, wherein a width of the distal tip is approximately the same as or less than a width of the catheter body.

Arrangement 25: The reentry catheter of any one of Arrangements 21-24, wherein the distal tip has an asymmetric shape such that the distal tip is more flexible in the first direction than in a third direction, wherein the third direction is opposite to the first direction.

Arrangement 26: The reentry catheter of any one of Arrangements 21-25, wherein the distal end portion of the distal tip is offset from a centerline of the distal tip by a distance that is from approximately 10% to approximately 50% of the diameter of the catheter body.

Arrangement 27: The reentry catheter of any one of Arrangements 21-26, wherein the port is configured to direct a guidewire that is advanced through the port to an angle that is from approximately 35 degrees to approximately 90 degrees relative to the axial centerline of the catheter body.

Arrangement 28: The reentry catheter of any one of Arrangements 21-27, further having a radiopaque marker adjacent to the distal port.

Arrangement 29: The reentry catheter of any one of Arrangements 21-28, further having a core member positioned in the distal tip configured to increase a bending stiffness of the distal tip in the second direction more than in the first direction.

Arrangement 30: The reentry catheter of any one of Arrangements 21-29, wherein the catheter body comprises one or more of single wire braiding, multi-wire braiding, coils, and any other suitable metal support structures.

Arrangement 31: The reentry catheter of any one of Arrangements 21-30, wherein the catheter body comprises one or more of single wire braiding, multi-wire braiding, coils, and any other suitable metal support structures made from stainless steel, tungsten, Co—Cr, or Ni—Ti.

Arrangement 32: The reentry catheter of any one of Arrangements 21-31, wherein a diameter of the catheter body is from approximately 2 Fr to approximately 6 Fr.

Arrangement 33: The reentry catheter of any one of Arrangements 21-32, further comprising a means for identifying an orientation of the distal tip in fluoroscopy.

Arrangement 34: The reentry catheter of any one of Arrangements 21-33, The reentry catheter of claim 13, further comprising a means for reducing the first stiffness of the distal tip in the first direction.

Arrangement 35: The reentry catheter of any one of Arrangements 21-34, The reentry catheter of claim 13, further comprising a means for deflecting a guidewire through the distal port.

Arrangement 36: A method of treating an occlusion in a blood vessel, comprising:

advancing a catheter having a catheter body into a patient's vasculature, the catheter having a distal tip that is configured to be more flexible in a first direction than in a second direction wherein the second direction is approximately orthogonal to the first direction, and a lumen extending through the catheter body;

advancing the distal tip toward a curve in the patient's vasculature;

rotating the catheter body to rotate the distal tip so that, as the distal tip is advanced against a wall of the vessel in the curve, the distal tip bends in the first direction, thereby better conforming to the curve of a wall of the vessel; and advancing the catheter body past the occlusion by advancing the distal tip of the catheter through a subintimal layer adjacent to the occlusion.

Arrangement 37: The method of Arrangement 36, further comprising advancing a guidewire through the lumen and out of a distal port in communication with the lumen so that an end of the guidewire is distal to the occlusion.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings. Embodiments of the present disclosure will now be described hereinafter, by way of example only, with reference to the accompanying drawings in which:

FIG. 1B also shows a guidewire extending from a distal portion of the reentry catheter after the reentry catheter has been advanced past the calcified lesion or hard plaque.

FIG. 22A is a section view of an embodiment of a portion of a distal tip that can be used with any catheter embodiments disclosed herein.

FIG. 22B is a section view of an embodiment of a portion of a distal tip that can be used with any catheter embodiments disclosed herein.

FIG. 22C is a section view of an embodiment of a portion of a distal tip that can be used with any catheter embodiments disclosed herein.

FIG. 22D is a section view of an embodiment of a portion of a distal tip that can be used with any catheter embodiments disclosed herein.

FIG. 22E is a section view of an embodiment of a portion of a distal tip that can be used with any catheter embodiments disclosed herein.

FIG. 22F is a section view of an embodiment of a portion of a distal tip that can be used with any catheter embodiments disclosed herein.

FIG. 22G is a section view of an embodiment of a portion of a distal tip that can be used with any catheter embodiments disclosed herein.

FIG. 22H is a section view of an embodiment of a portion of a distal tip that can be used with any catheter embodiments disclosed herein.

FIG. 28A is an end view of a distal portion of another catheter embodiment.

FIG. 28B is a side end view of the distal portion of the catheter embodiment shown in FIG. 28A.

FIG. 29A is an end view of a distal portion of another catheter embodiment.

FIG. 29B is a side end view of the distal portion of the catheter embodiment shown in FIG. 29A.

FIG. 30 is a side view of a distal portion of another catheter embodiment.

FIG. 31A illustrates a catheter having a straight (but tapered) catheter tip being advanced through a vessel lumen.

FIG. 31B illustrates a catheter having a curved (and tapered) catheter tip being advanced through a vessel lumen.

FIG. 38 is a side view of a distal portion of another catheter embodiment.

FIG. 39 is cross-sectional view of the catheter embodiment shown in FIG. 38, taken through line 39-39 shown in FIG. 38.

FIG. 40 is a side view of a distal portion of another catheter embodiment.

FIG. 41 is cross-sectional view of the catheter embodiment shown in FIG. 40, taken through line 41-41 shown in FIG. 40.

FIG. 42 is cross-sectional view of the catheter embodiment shown in FIG. 40, taken through line 41-41 shown in FIG. 40.

FIG. 43 is a side view of a distal portion of another catheter embodiment.

FIG. 44 is a side view of a distal portion of another catheter embodiment.

DETAILED DESCRIPTION

Embodiments of systems, components and methods of assembly and manufacture will now be described with reference to the accompanying figures, wherein like numerals refer to like or similar elements throughout. Although multiple embodiments (also referred to herein as arrangements, such that the terms arrangements and embodiments are meant to be interpreted to be synonymous), examples, and illustrations are disclosed herein, it will be understood by those of ordinary skill in the art that the inventions described herein extend beyond the specifically disclosed embodiments, examples, and illustrations disclosed herein and can include other uses of the inventions and obvious modifications and equivalents thereof, and combinations of any of the embodiments or the components, features, and/or details of any of the embodiments disclosed herein. Additionally, it should be noted that the descriptions of all of the embodiments disclosed herein should be interpreted to include any of the features, components, and other details of any of the other embodiments disclosed here in combination with or in the alternative to any of the features, components, and other details explicitly described herein. Therefore, any embodiments of the reentry catheters or components thereof disclosed herein can have any of the features, components, and/or other details of any of the other reentry catheter embodiments or components thereof disclosed herein, including the catheter embodiments and components thereof recited in the claims, to form additional embodiments having any combination of any of the features disclosed herein.

Figure 1A:
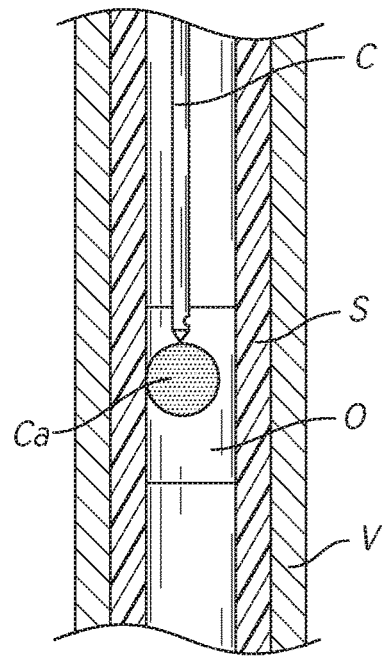
FIG. 1A shows an embodiment of a reentry catheter advancing through a blood vessel in the region of an occlusion having a calcified lesion or hard plaque.
Figure 1B:
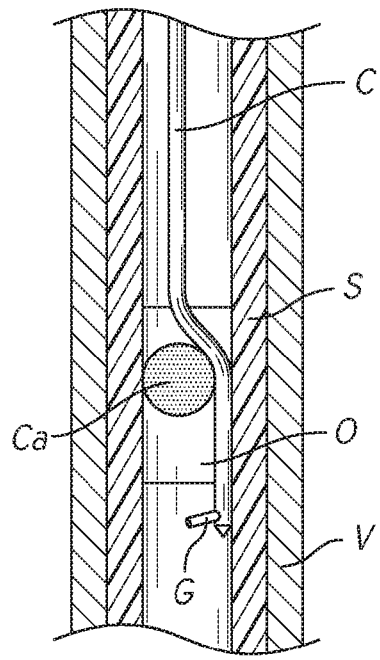
FIG. 1B shows the embodiment of the reentry catheter of FIG. 1A navigating around the calcified lesion or hard plaque wherein the reentry catheter has been advanced adjacent to, but not penetrating, the sub intimal layer.
Figure 1C:
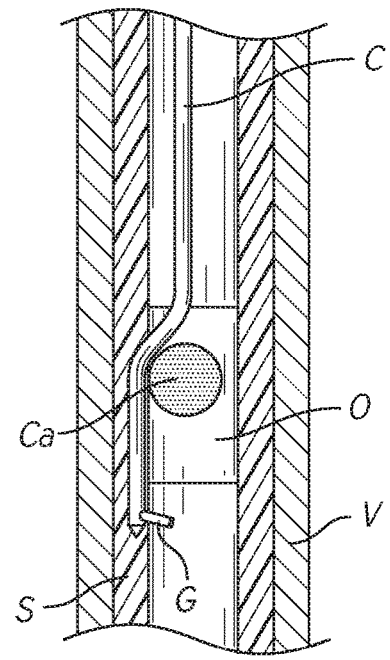
FIG. 1C shows a guidewire extending from a distal portion of the embodiment of the reentry catheter of FIG. 1A after the distal portion of the reentry catheter has been advanced past the calcified lesion or hard plaque.

Embodiments of the devices disclosed herein can have a catheter, referred to herein as a reentry catheter that can be used to bypass occlusions. Because bypassing a chronic total occlusion (CTO) using a guidewire presents so many difficulties and patient risks, the embodiments of the devices and methods disclosed herein were developed to enable a surgeon to cross or advance past a CTO without using a guidewire to do so. Embodiments of the reentry catheters disclosed herein can be configured to track or be advanced past occlusions adjacent to or within the subintimal portion of the vessel wall, as illustrated in FIGS. 1A-1C. In particular, FIG. 1A shows an embodiment of a reentry catheter C advancing through a blood vessel V having a subintimal layer S in the region of an occlusion O having a calcified lesion or hard plaque Ca. FIG. 1B shows the embodiment of the reentry catheter C of FIG. 1A navigating around the calcified lesion or hard plaque Ca wherein the reentry catheter C has been advanced adjacent to, but not penetrating, the sub intimal layer S. FIG. 1B also shows a guidewire G extending from a distal portion of the reentry catheter C after the reentry catheter C has been advanced past the calcified lesion or hard plaque Ca. FIG. 1C shows a guidewire G extending from a distal portion of the embodiment of the reentry catheter C after the distal portion of the reentry catheter C has been advanced past the calcified lesion or hard plaque Ca.

Embodiments presented herein address significant shortcomings and problems of the currently available reentry guidewires and catheters, including the increased risk of vessel wall rupture, the difficulty and time-consuming nature of manipulating conventional guidewires and catheter devices in the region of the occlusion, etc. The reentry catheter embodiments disclosed herein produce a range of performance and usability advantages over the presently available catheters.

Figure 2A:
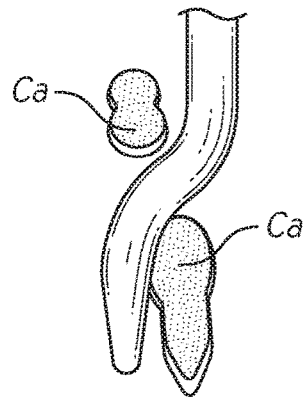
FIG. 2A illustrates an embodiment of a reentry catheter as disclosed herein being maneuvered around calcified lesions that may be present in a patient's vascular system.
Figure 2B:
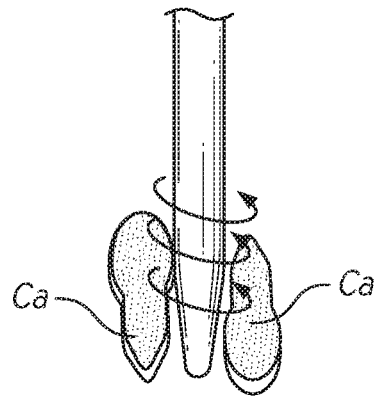
FIG. 2B illustrates the improved rotatability and/or torquability of any of the reentry catheter embodiments disclosed herein to penetrate calcified lesions.
Figure 2C:
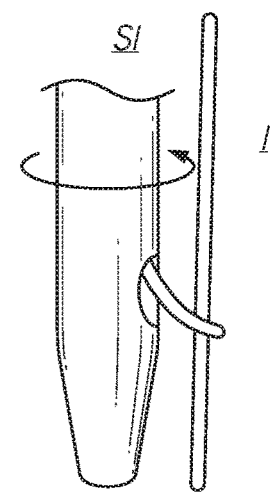
FIG. 2C illustrates a guidewire being extended through an opening in any of the reentry catheter embodiments disclosed herein and advancing into the intimal space from the subintimal space.

FIGS. 2A-2C illustrate some nonlimiting examples of the procedures and/or capabilities of any of the reentry catheter embodiments disclosed herein. For example, FIG. 2A illustrates an embodiment of a reentry catheter as disclosed herein being maneuvered around calcified lesions Ca that may be present in a patient's vascular system. FIG. 2B illustrates the improved rotatability and/or torquability of any of the reentry catheter embodiments disclosed herein to penetrate calcified lesions Ca. FIG. 2C illustrates a guidewire being extended through an opening in any of the reentry catheter embodiments disclosed herein and advancing into the intimal space I from the subintimal space SI.

In any embodiments (which is meant to include, without limitation, any embodiments disclosed and/or incorporated by reference herein and any variants of such that would be readily apparent or obvious to one of ordinary skill in the art), the reentry catheter can have an elongate body or shaft, a lumen substantially or completely through a length of the catheter shaft, and a flexible distal tip positioned at a distal end of the catheter shaft. Further, any embodiments can have a connector or hub assembly positioned at or adjacent to a proximal end of the catheter body. The hub assembly can have internal threads and/or any configuration suitable for connecting with any other medical components.

In any embodiments, the distal tip can be solid in cross section along the entire length of the distal tip. In some embodiments, the distal tip can have a lumen through all or a portion of the distal tip. The lumen can be in communication with the catheter body lumen extending through all or part of the catheter body. A side hole or port can be formed in the distal tip at the distal end of the lumen, with the side hole formed at an angle relative to the lumen for directing a guidewire out of the lumen at a desired angle relative to the axial centerline of the catheter body. In any embodiments disclosed herein, the catheter can be configured to direct the guidewire advancing out of the side hole at an angle of approximately 35 degrees relative to the longitudinal axis of the centerline of the catheter body, or from approximately 25 degrees to approximately 50 degrees, or from and to any angles within that range.

Additionally, in embodiments where the lumen does not extend into the distal tip of the catheter, the catheter body can have a side hole extending through a side wall of the catheter body. The side hole can be angled relative to the lumen and being configured to direct a guidewire out of the lumen at an angle relative to a longitudinal axis of the catheter body. The hole can be located and formed to be in communication with the lumen extending through all or part of the catheter body. More details about each of these features or components will be described herein.

In any embodiments, the catheter can comprise any suitable materials, including without limitation urethane, polyamide (PEBAX), and/or any other suitable polymer or combination of the foregoing. In any embodiments, the catheter shaft can be braided or unbraided. Further, any embodiments of the catheter can have one or more coils, cable tubes, and/or any other suitable metal support structure or combination of the foregoing desired along any portion of the length of the catheter body. One or more of the braids or coils in any embodiments can be made from any suitable material, including without limitation, stainless steel, tungsten, Co—Cr, or Ni—Ti. The braids or coils can be made from a single wire, multiple wires, or otherwise.

Any embodiments of the reentry catheter disclosed herein can have coil and/or braid reinforcement at any position or portion of the catheter body, including a distal end portion of the catheter body. The coil or braid can be made from any suitable metal or plastic. The wire can be round, flat/ribbon, multi-filar, or of any other suitable configuration. Depending on the size of the tube and the wall available, approximately 0.001" to 0.0015" stainless steel round or thick wires in the form of braid or coil can be used for reinforcement. The use of wire coil can give better flexibility and result in the reduced diameters needed to perform CTO procedures. Similarly and alternatively, polymer fiber such as Radel, Dacron, and Kevlar can also be used for reinforcement, in combination with and or in place of any of the other reinforcement materials in any of the embodiments disclosed herein.

In some embodiments, though not required, the catheter can have an inner layer. The inner layer can be formed from any suitable fluoroplastic material, for example PTFE or otherwise. In some embodiments, the catheter can have an outer layer. The outer layer of the catheter body can be made from nylon, PEBAX, polyester, polyurethane, or any other suitable materials. Additionally, the catheter body and/or distal tip can have coatings on an outside surface and/or an inside surface. The coating material can be hydrophilic or hydrophobic, and can promote lubricity.

The diameter of any catheter body embodiments disclosed herein can be approximately 3 Fr, or from approximately 2 Fr to approximately 6 Fr, or to and from any values within this range. The catheter body can be configured to be compatible with a guidewire that is approximately 0.035 in diameter, or from approximately 0.010 in to approximately 0.038 in, or to and from any values within this range. Other embodiments can be configured to receive larger or smaller diameter guidewires. Any embodiments of the catheter body can be configured to be bendable, so as to be capable of following tortuous vessels, such as peripheral vessels, without causing puncture or perforation. Additionally, any of the catheter embodiments disclosed herein can be optimized for good torquability.

Figure 3:
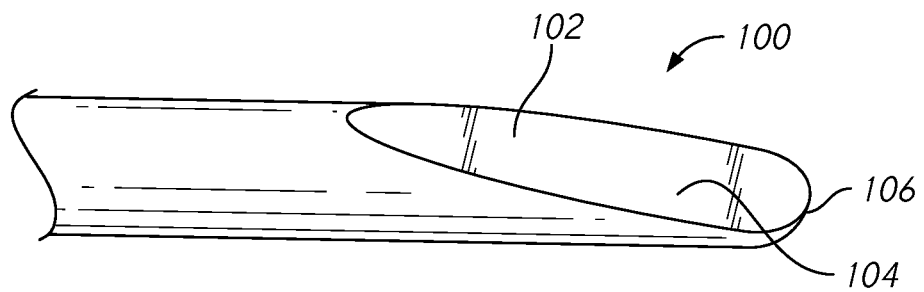
FIG. 3 is an illustration of a distal portion of an embodiment of a catheter having distal tip that can be used with any of the catheter embodiments disclosed here.

Embodiments of the reentry catheter disclosed herein can have a flexible distal tip, or a distal tip made generally of a soft material. A rigid distal tip can increase the risk of puncturing the penetrate vessel wall. FIG. 3 is an illustration of a distal end portion of an embodiment of a catheter 100 having distal tip 102 that can be used with any of the catheter embodiments disclosed here. As shown in FIG. 3, the distal tip 102 can have an angled or tapered top surface 104 (also referred to as an angled portion) and a rounded distal edge 106. Any embodiments can have an angled bottom surface also. In any embodiments, the distal edge can be flat, angled, triangular, or have any desired shape. The distal tip can be made from any suitable, generally flexible and biocompatible material, such as a biocompatible polymer like polyurethane.

In any embodiments, the top surface 104 (which can be angled, beveled, or otherwise shaped or configured) of the distal tip 102 can have a length from approximately 0.020 in (0.5 mm) to approximately 0.79 in (20 mm), depending on the configuration, the flexibility of the tip desired (a longer angled portion 104 can result in a more flexible distal tip), the application, and other factors. In any embodiments, a thickness of the distal end of tapered flat blade tip can be greater than or equal to approximately 0.002 in (0.05 mm) and less than or equal to a diameter of the shaft.

Figure 4:
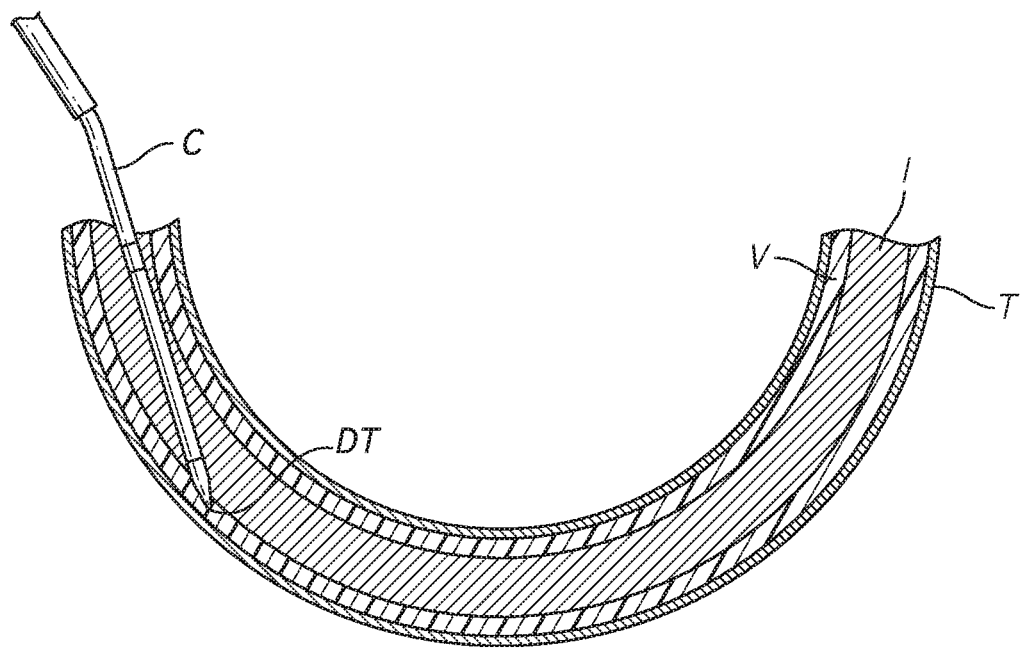
FIG. 4 illustrates a laboratory test set up illustrating the performance of a conventional catheter advancing through a curve portion of a vessel wall.

FIG. 4 is an illustration of a laboratory test that was performed, showing a rigid distal tip (DT) being advanced through a simulated intimal layer substance. FIG. 4 illustrates a laboratory test set up illustrating the performance of a conventional catheter advancing through a curve portion of a vessel wall. The test setup simulates an inner layer I and a vessel wall V. A plastic tube T is used to support the substance used to simulate the inner layer I and the vessel wall V. In the laboratory setup, the intimal layer I substance was simulated by using gel having a higher hardness than a typical soft gel, for example, 2.5 times harder than a typical soft gel. The gel used for the intimal layer I in the illustrated test setup was a composition of agarose having a 1-2 weight percent. The gel used to simulate the vessel wall V was made from a composition of agarose having a 4-6 weight percent.

Figure 5:
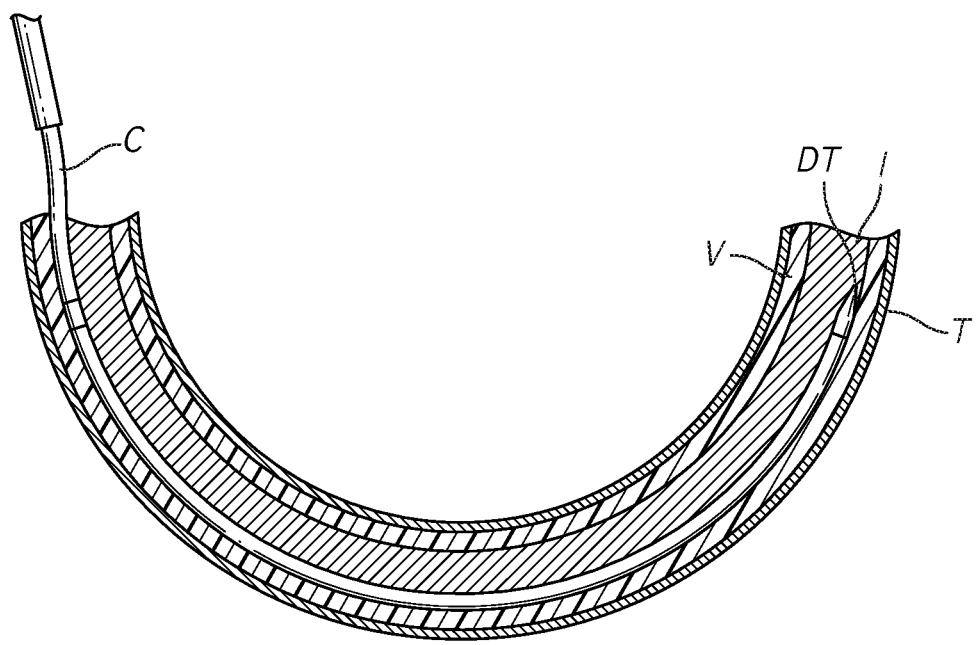
FIG. 5 illustrates a laboratory test set up illustrating the performance of a embodiment of a reentry catheter as disclosed herein advancing through a curve portion of a vessel wall.

As shown in FIG. 4, a conventional, rigid distal tip penetrates the simulated vessel wall, and is unusable for a CTO procedure due to the associated risks of such a penetration. FIG. 5 shows the result of a flexible distal tip that has been advanced through the simulated vessel. As shown, the flexible distal tip shown in FIG. 5 has been successfully advanced through the simulated curved vessel V without ever penetrating the vessel wall V.

Figures 6A, 6B:
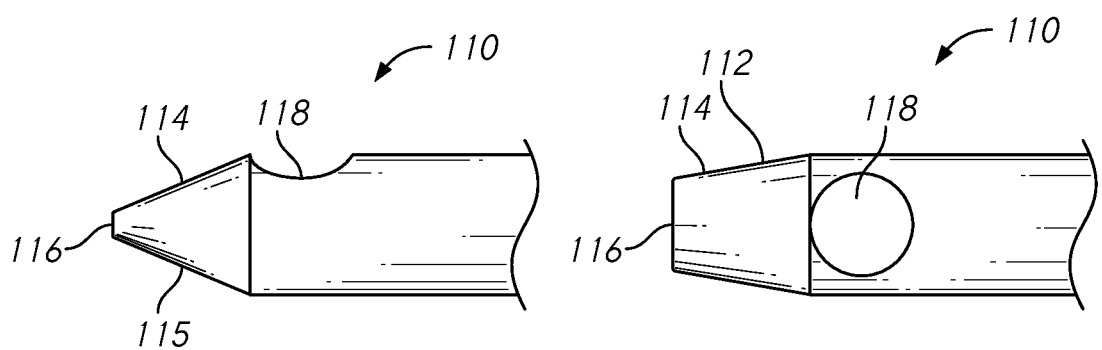
FIG. 6A is a side view of an embodiment of a reentry catheter.
FIG. 6B is a top view of the reentry catheter embodiment shown in FIG. 6A.
Figure 6C:
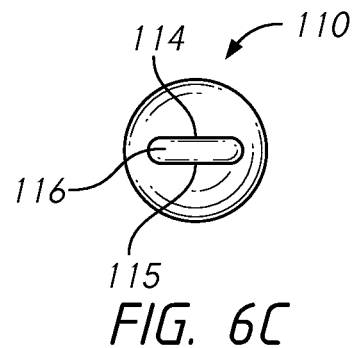
FIG. 6C is an end view of the reentry catheter embodiment shown in FIG. 6A.

FIGS. 6A, 6B, and 6C are a side view, top view, and end view, respectively, of an embodiment of a reentry catheter 110 having a flexible distal tip 112. The distal tip 112 can have an angled top surface 114, an angled bottom surface 115 and a distal or leading edge 116. In any embodiments, the top and bottom angled surfaces can be symmetric about a center plane the goes through the axial center of the catheter tip, such that the top and bottom surfaces are generally the same, but opposing. However, in any embodiments, the top and bottom angled surfaces can be different such that the distal tip is asymmetric about the center plane the goes through the axial center of the catheter tip. Additionally, as shown in FIGS. 6A-6C, any embodiments of the reentry catheter can have a distal port or hole 118 formed through either the catheter body or the distal tip, or partially through both the catheter wall and the distal tip. The distal port 118 can be in communication with a lumen extending through the catheter body.

Any distal tip embodiments disclosed herein can be more flexible in one direction (for example, a first direction, such as the upward and/or downward direction in FIG. 6A) than in a second direction that is generally orthogonal to the first direction (with reference to FIG. 6B the second direction is, for example, the lateral directions which are in the upward and downward directions in the top view of FIG. 6B). For example and without limitation, any of the embodiments disclosed herein can be configured so that the distal end of the distal tip is approximately 100% more flexible in the first direction (i.e., upward and/or downward direction) than in the second or lateral direction (i.e., so that the distal tip is approximately twice as flexible in the upward or downward direction than in the lateral direction), or from approximately 50% (alternatively, less than 50%) to approximately 300% (alternatively, more than 300%) more flexible in the first direction than in the second direction, or from approximately 100% to approximately 200% more flexible in the first direction than in the second direction.

In any embodiments disclosed herein, though not required, a length of the angled top and/or bottom surface of the distal tip can be from approximately 0.039 in (1 mm) to approximately 0.47 in (12 mm). For example and without limitation, a 2 Fr catheter can have a distal tip having an angled top and/or bottom surface having a length that is from approximately 0.039 in (1 mm) to approximately 0.16 in (4 mm), a 3 Fr catheter can have a distal tip having an angled top and/or bottom surface having a length that is from approximately 0.079 in (2 mm) to approximately 0.24 in (6 mm), a 4 Fr catheter can have a distal tip having an angled top and/or bottom surface having a length that is from approximately 0.12 in (3 mm) to approximately 0.31 in (8 mm), a 5 Fr catheter can have a distal tip having an angled top and/or bottom surface having a length that is from approximately 0.12 in (3 mm) to approximately 0.39 in (10 mm), and a 6 Fr catheter can have a distal tip having an angled top and/or bottom surface having a length that is from approximately 0.12 in (3 mm) to approximately 0.47 in (12 mm).

Additionally, in any embodiments disclosed herein, the distal tip of the catheter can be configured such that, at any point along a length of the distal tip, the second moment of area can be calculated for both the vertical (or first) direction and the widthwise or lateral direction (also referred to herein as the second direction) to determine the relative stiffness of the catheter tip along the length of the catheter tip in the vertical and the lateral directions. In any embodiments disclosed herein, the distal tip can have a second moment of area in the lateral direction that is at least approximately 60 times greater than the second moment of area in the vertical direction at a distal portion of the distal tip, is from approximately 5 to approximately 8 times greater at one-quarter of the length of the distal tip from the distal end, is approximately 2 to approximately 3 times greater at a mid portion of the distal tip, and is from approximately 1 to approximately 2 times greater at the approximately three-quarter point of the length of the distal tip from the distal end.

Figure 7A:
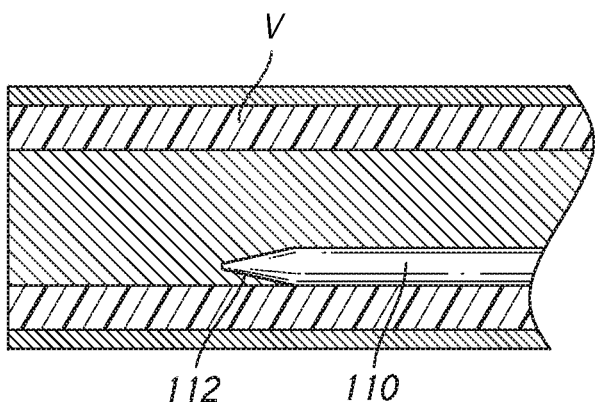
FIG. 7A is a side view of another embodiment of a reentry catheter.
Figure 7B:
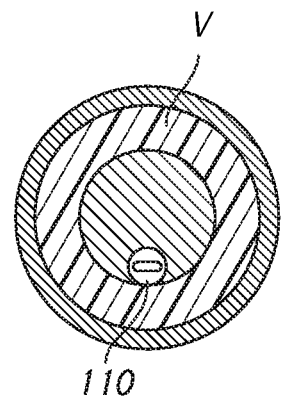
FIG. 7B is an end view of the reentry catheter embodiment shown in FIG. 7A.
Figure 7C:
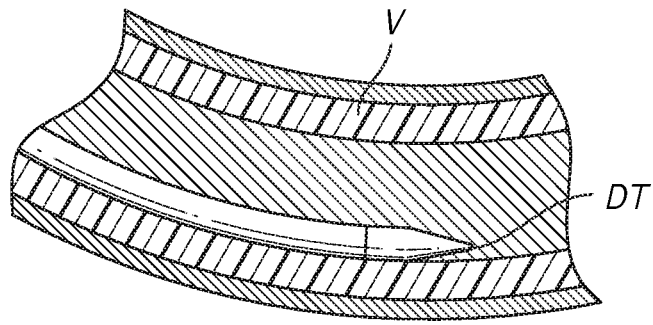
FIG. 7C is a side view of the reentry catheter embodiment shown in FIG. 7A being advanced along a curved portion of the vessel wall.

FIGS. 7A-7C show another embodiment of a reentry catheter 110 having a distal tip 112 (which can be flexible and can have a symmetrically shaped and angled distal end portion), showing the catheter 110 as the catheter 110 and distal tip 112 are advanced along the intimal boundary of the vessel wall V.

Figure 8A:
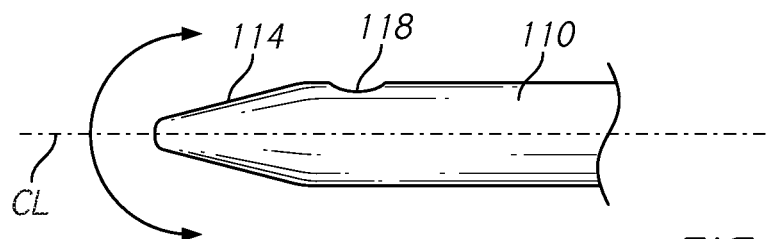
FIG. 8A is a side view of an embodiment of a distal tip portion that can be used with any reentry catheter embodiment disclosed herein.
Figure 8B:
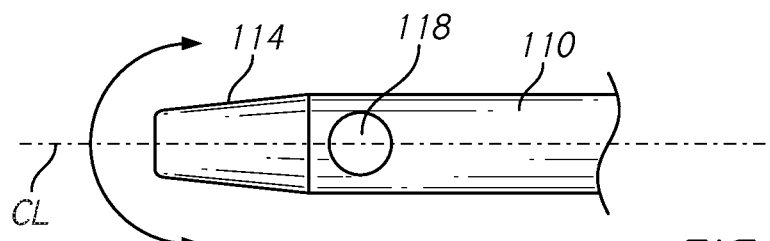
FIG. 8B is a top view of the distal tip portion shown in FIG. 8A.
Figure 9A:
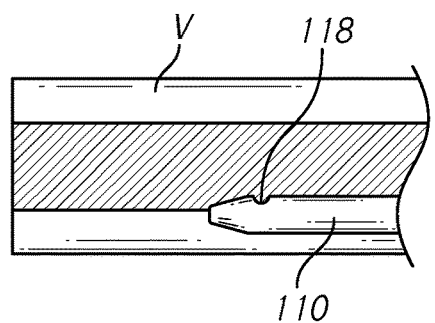
FIG. 9A is a side view of an embodiment of a reentry catheter being advanced along a length of a vessel in a sub intimal portion of the vessel.
Figure 9B:
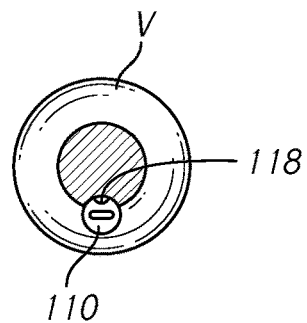
FIG. 9B is an end view of FIG. 9A.
Figure 10A:
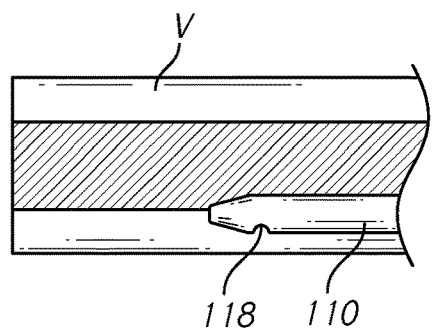
FIG. 10A is a side view of the embodiment of the reentry catheter of FIG. 9A with the distal port facing radially outward.
Figure 10B:
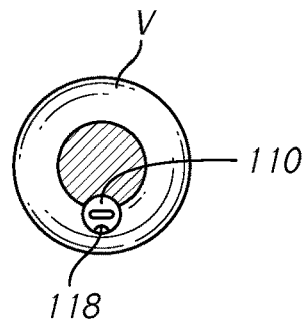
FIG. 10B is an end view of FIG. 10A.

With reference to FIGS. 8A and 8B, in any embodiments disclosed herein, the distal tip 112 can be sized and configured to be more flexible about the centerline axis CL in the up and down direction (shown in FIG. 8A) than in the lateral direction (shown in FIG. 8B). In this configuration, when the distal tip 112 is oriented properly (i.e., such that the angled surface of the distal tip is facing radially outward), the greater flexibility of the distal tip in the up and down direction can improve the ability of the distal tip be maintain its position in the subintimal region of the vessel, as shown in FIGS. 9A-9B, even in curved anatomy. Optimally, for some procedures, the distal port 118 will be positioned radially inward so that a guidewire advanced through the catheter body will be advanced radially inwardly as the guidewire is advanced through the distal port. FIGS. 10A-10B show the embodiment of the catheter 110 oriented with the distal port 118 facing radially outwardly. The surgeon or medical practitioner need only twist the catheter body so that the distal port 118 rotates 180 degrees, to face inwardly, if desired to advance the guidewire into the intimal space of the vessel.

Figure 11:
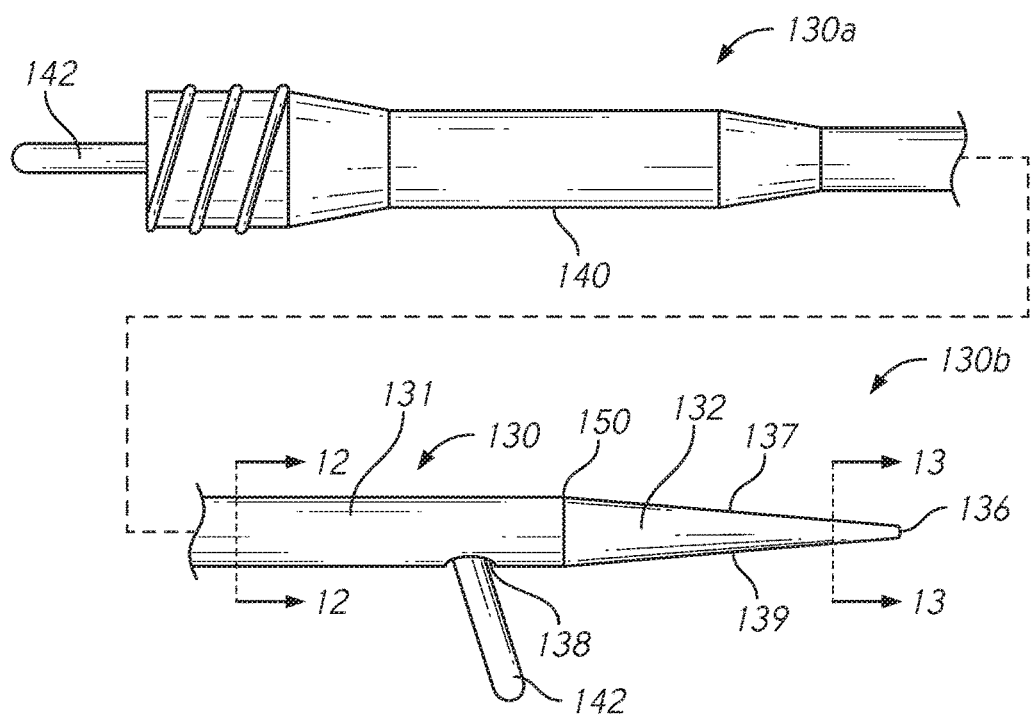
FIG. 11 is a side view of another embodiment of a reentry catheter.

As discussed above, in any catheter embodiments disclosed herein, the distal tip can have a generally tapered leading portion, wherein the main features of the taper are in the vertical direction (for example, as in catheter embodiment 110 shown in FIG. 8A). For example without limitation, FIG. 11 shows a side view of another embodiment of a catheter 130 having a catheter body 131, a distal tip 132, and a hub or connector element 140. The hub element can be located at a proximal end 130a of the catheter 130, and the distal tip 132 can be located at a distal end 130b of the catheter 130. The embodiment of the catheter 130 can have any of the other features, components, or other details of any of the other embodiments disclosed herein, in combination with or in place of any of the features, components, or other details disclosed with respect to the catheter 130 to form new embodiments. Similarly, any of the other embodiments disclosed herein can have any of the features, components, or other details described herein with respect to the catheter 130 in combination with or in place of any of the features, components, or other details disclosed with respect to the embodiment of the other catheter.

A guidewire 142 can be advanced through a lumen formed in the catheter body from the proximal end 130a of the catheter 130 and exit through a distal port 138. In some embodiments, the distal tip can be formed monolithically or of the same materials as the catheter body. In some embodiments, the distal tip can be formed separately from the catheter body and joined together with the catheter body at approximately joint 150.

The distal tip 132 can have leading edge 136, an angled top surface 137, and an angled bottom surface 139. In any distal tip embodiments disclosed herein, including without limitation distal tip 132, the top surface (or first surface) and the bottom surface (or second surface) can be planar or flat, though at a tapering angle, as is illustrate in FIGS. 11-13. In any embodiments, the top and bottom angled surfaces 137, 139 can be symmetric about a center plane that goes through the axial center of the catheter tip, such that the top and bottom surfaces are generally the same, but opposing. However, in any embodiments, the top and bottom angled surfaces can be different such that the distal tip is asymmetric about the center plane that goes through the axial center of the catheter tip. Additionally, as shown in FIG. 11, any embodiments of the catheter 130 can have a distal port or hole 138 formed through either the catheter body or the distal tip, or partially through both the catheter wall and the distal tip. The distal port 138 of the catheter 130 is formed through the catheter body 131. In any embodiments, the distal port 138 can be in communication with a lumen extending through the catheter body 131.

Figure 12:
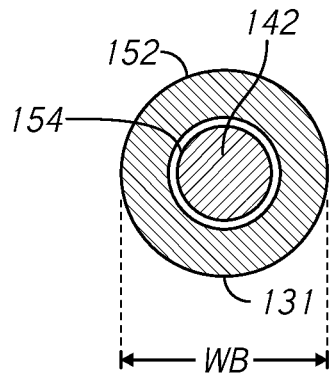
FIG. 12 is cross-sectional view of the reentry catheter embodiment shown in FIG. 11, taken through line 12-12 shown in FIG. 11.
Figure 13:
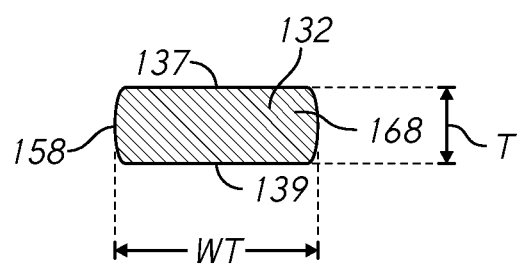
FIG. 13 is cross-sectional view of the reentry catheter embodiment shown in FIG. 11, taken through line 13-13 shown in FIG. 11.

FIG. 12 is cross-sectional view of the catheter body 131, taken through line 12-12 shown in FIG. 11. FIG. 13 is cross-sectional view of the distal tip 132 of the embodiment of the catheter body 131, taken through line 13-13 shown in FIG. 11. With reference to FIG. 12, the catheter body 131 can have a generally round outer surface 152, and a generally round shaped lumen 154 extending therethrough. As described, a guidewire 142 can be advanced through the lumen 154.

With reference to FIG. 13, the top angled surface 137 of the distal tip can be generally linear or flat in the horizontal direction. The bottom angled surface 139 of the distal tip can also be generally linear or flat in the horizontal direction. The distal tip 132 can have a first side surface 158 and a second side surface 168. In any embodiments, the first and second side surfaces 158, 168 can be flat, curved, or otherwise. In the illustrated embodiment, the first and second side surfaces 158, 168 are curved, and can be sized and configured to match the same profile or diameter of the outer surface 152 of the catheter body 131.

The outer surface 152 can have a width in a lateral direction represented by WB in FIG. 12. The distal tip 132 can have a width in a lateral direction represented by WT in FIG. 12. In any embodiments, the width WT in the lateral direction of the distal tip 132 can be approximately the same along the entire length of the distal tip 132. Alternatively, in any embodiments, the distal tip 132 can also taper in the lateral direction along the length of the distal tip 132. For example and without limitation, in some embodiments, the width WT of distal tip 132 can be greatest adjacent to a proximal end 150 of the distal tip, and less or the least at the distal end 136 of the distal tip 132. Additionally, the distal tip 132 can have a thickness in a vertical direction represented by T in FIG. 12. In any embodiments, the width WT at the distal end can be approximately 0.004 in (0.1 mm) or greater.

Figure 14:
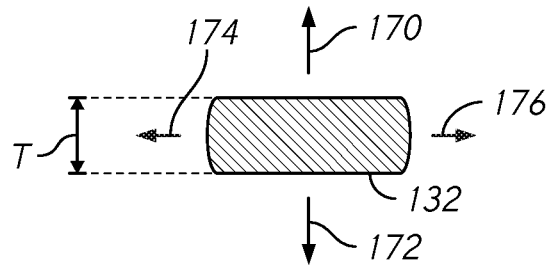
FIG. 14 is cross-sectional view of the reentry catheter embodiment shown in FIG. 11, taken through line 13-13 shown in FIG. 11, and illustrates relative flexibility of the distal tip in different directions.

FIG. 14 shows a cross-section of the distal tip 132, also taken along line 13-13 of FIG. 11. FIG. 14 illustrates the degree or extent of flexibility of the distal tip at section 13-13, illustrating that the tip is more flexible in the upward and downward directions 170, 172 respectively than the tip is in the first lateral direction 174 or the second lateral direction 176. In this configuration, because the distal tip 132 is symmetrical both in the vertical and horizontal directions, the degree or amount of flexibility of the distal tip 132 at section 13-13 is the same in the upward direction 170 as it is in the downward direction 172. Similarly, in some embodiments, the degree or amount of flexibility can be the same in the first lateral direction 174 as it is in the second lateral direction 176. In any embodiments, the tip can be at least approximately twice as flexible in the upward and downward directions 170, 172 as the distal tip 132 is in the first and second lateral directions 174, 176, or approximately three to approximately five times more flexible in the upward and downward directions 170, 172 as the tip is in the first and second lateral directions 174, 176.

Figure 15:
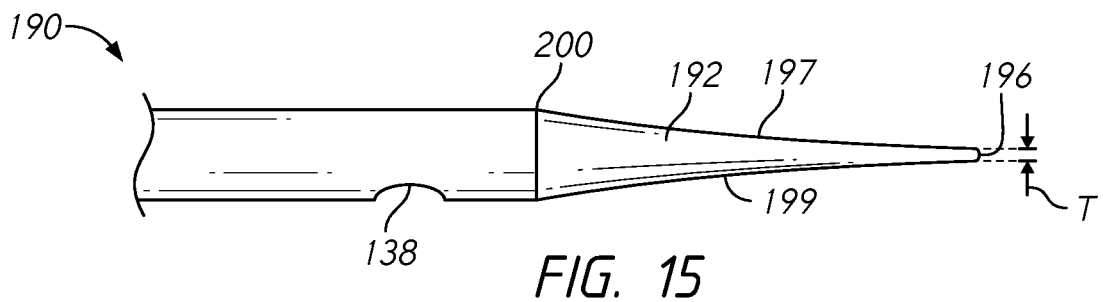
FIG. 15 is a side view of a distal portion of another embodiment of a catheter body.

FIG. 15 is a side view of a distal portion of another embodiment of a catheter body 190 having a distal tip 192. As shown in FIG. 15, the distal tip 192 can have a curved top surface 197 (which can be concave) and a curved bottom surface 199 (which can be convex). The top and bottom surfaces can be formed at a constant radius, can be parabolic, or can have any desired curved profile, such as a progressive radius wherein the radius changes along a length of the distal tip 192, or otherwise. In any distal tip embodiments disclosed herein, a thickness T in a vertical direction of the distal tip (such as distal tip 192) can increase along a length of the distal tip from a distal end portion (such as end portion 196) of the distal tip (such as distal tip 192) to the proximal end portion (such as proximal end portion 200) of the distal tip. In the illustrated embodiment, the change or increase in the thickness T in the vertical direction of the distal tip 192 is more gradual adjacent to the distal end portion 196. The change or increase in the thickness T in the vertical direction of the distal tip 192 progressively increases along the length of the distal tip 192 from the distal end portion 196 to the proximal end portion 200, wherein the change in thickness is greatest near the proximal end portion 200.

Figure 16:
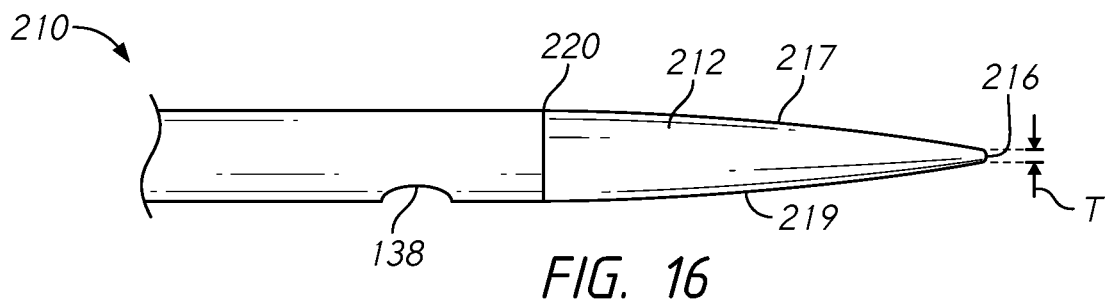
FIG. 16 is a side view of another embodiment of a catheter body.

FIG. 16 is a side view of another embodiment of a catheter body 210 having a distal tip 212. As shown in FIG. 15, the distal tip 212 can have a curved top surface 217 (which can be convex) and a curved bottom surface 219 (which can be concave). The top and bottom surfaces can be formed at a constant radius, can be parabolic, or can have any desired curved profile, such as a progressive radius wherein the radius changes along a length of the distal tip 212, or otherwise. In any embodiments disclosed herein, a thickness T in a vertical direction of the distal tip 212 can increase along a length of the distal tip from a distal end portion 216 of the distal tip 212 to the proximal end portion 220 of the distal tip 212. In the illustrated embodiment, the change or increase in the thickness T in the vertical direction of the distal tip 212 is more gradual adjacent to the proximal end portion 220. The change or increase in the thickness T in the vertical direction of the distal tip 212 progressively decreases along the length of the distal tip 212 from the distal end portion 216 to the proximal end portion 220, wherein the change in thickness is greatest near the distal end portion 216

Figure 17:
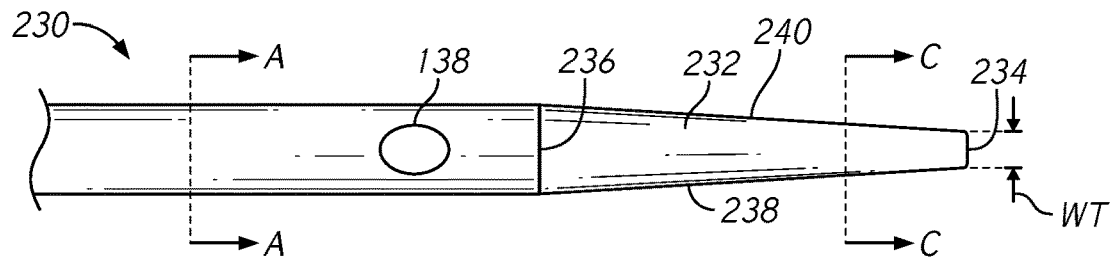
FIG. 17 is a top view of a distal portion of another catheter embodiment.

FIG. 17 is a top view of a distal end portion of another embodiment of a catheter 230. As mentioned, in any embodiments, the distal tip can be tapered in the widthwise direction so that a width WT can change along all or a portion of the length of the distal tip. For example, with reference to FIG. 17, the embodiment of the catheter 230 can have a distal tip 232 that has a tapered width along an entire length of the distal tip 232 from a distal portion or end 234 to a proximal portion or end 236 of the distal tip 232. As shown, a first side 238 and a second side 240 can have a linear or straight taper along the entire length of the distal tip 232. In this configuration, a width WT of the distal tip 232 can increase linearly from the distal tip portion 234 along the entire length of the distal tip 232 to the proximal tip portion 236. In this configuration, the tapered side walls 238, 240 of the distal tip 232 contribute to the distal tip 232 being even more flexible in the distal portions of the distal tip 232 relative to the proximal portions of the distal tip 232.

Figure 18:
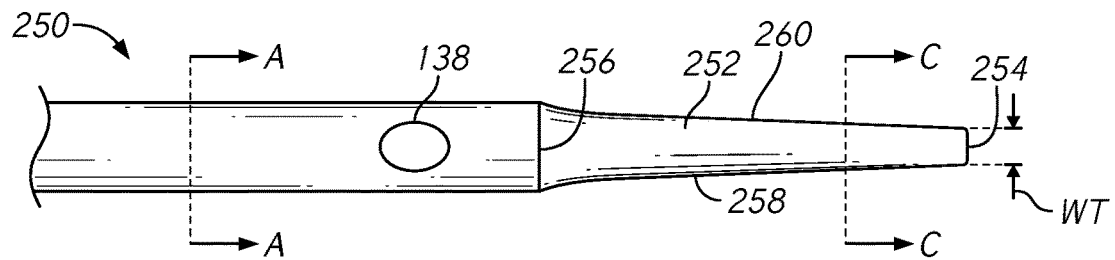
FIG. 18 is a top view of a distal portion of another catheter embodiment.

FIG. 18 is a top view of a distal end portion of another embodiment of a catheter 250. As shown in FIG. 18, the distal tip can have curved sidewalls 258, 260 that are curved along a portion of, or along the entire length of, the distal tip 252. The curvature of the sidewalls 258, 260 can have a constant radius, can be parabolic, or can have a progressive radius that changes along the length of the distal tip 252. In some embodiments, as in the illustrated embodiment, the change in width WT of the distal tip 252 having curved sidewalls 258, 260 can increase along a length of the distal tip 252 from the distal end portion 254 to the proximal end portion 256 of the distal tip 252 such that the greatest change in width WT of the sidewalls occurs closest to the proximal end 256 of the distal tip 252.

Figure 19:
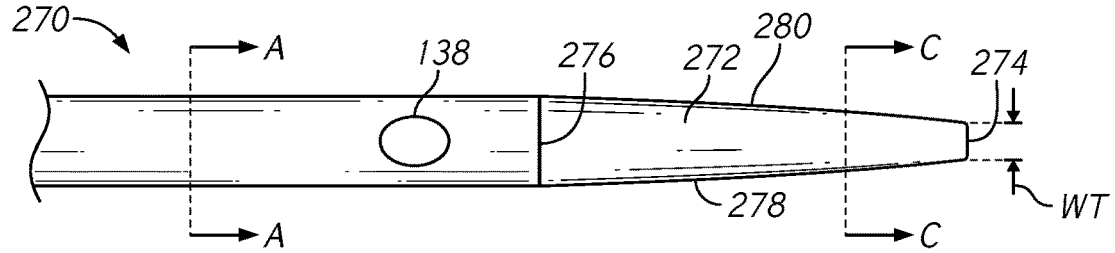
FIG. 19 is a top view of a distal portion of another catheter embodiment.

FIG. 19 is a top view of a distal end portion of another embodiment of a catheter 270. As shown in FIG. 19, the distal tip can have curved sidewalls 278, 280 that are curved along a portion or the entire length of the distal tip 272. The curvature of the sidewalls 278, 280 can have a constant radius, can be parabolic, or can have a progressive radius that changes along the length of the distal tip. In some embodiments, as in the illustrated embodiment, the change in width WT of the distal tip 272 having curved sidewalls 278, 280 can decrease along a length of the distal tip 272 from the distal end portion 274 to the proximal end portion 276 of the distal tip 272 (while the width WT increases) such that the greatest change in width WT of the sidewalls occurs closest to the distal end 274 of the distal tip 272.

Figure 20:
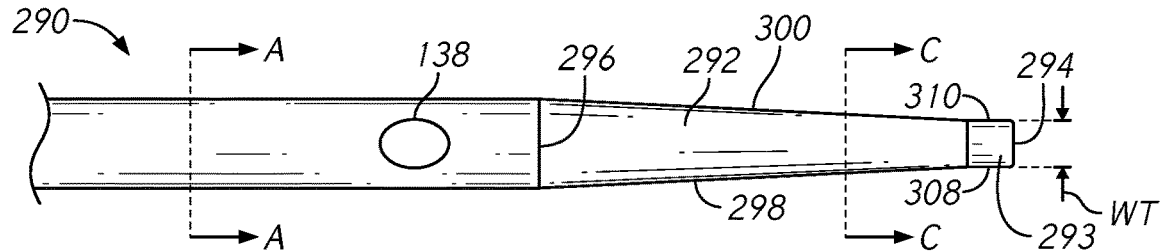
FIG. 20 is a top view of a distal portion of another catheter embodiment.
Figure 21:
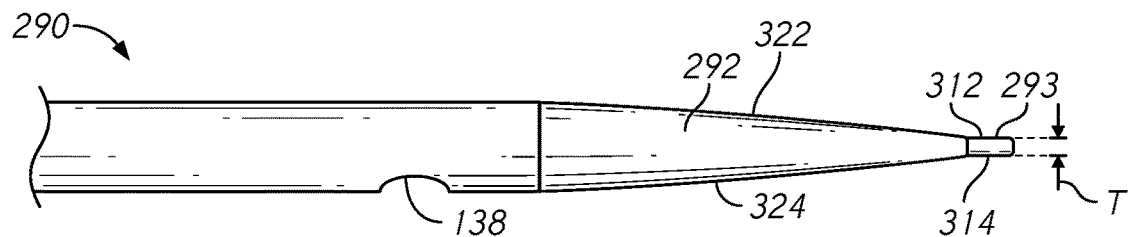
FIG. 21 is a side view of a distal portion of the catheter embodiment shown in FIG. 20.

FIG. 20 is a top view of a distal end portion of another embodiment of a catheter 290 having a tapered distal tip 292. FIG. 21 is a side view of the distal end portion of the embodiment of the catheter 290 illustrated in FIG. 20. Any catheter embodiments disclosed herein, including without limitation catheter 290, can have a distal tip portion 293 that has a different vertical and/or widthwise profile as compared to the rest of the distal tip 292. For example and without limitation, the distal tip portion 293 can have parallel, non-tapered sidewalls 308, 310 that have a different profile than the sidewalls 298, 300, which tapered sidewalls 298, 300 can be straight tapered, or have a curved tapered profile, or any other profile disclosed herein or desired. In any embodiments, the sidewalls 308, 310 can be straight so as to have no change in width WT along the length of the distal tip portion 293, or can be tapered and have the same taper as the tapered sidewalls 298, 300, or have a different taper as compared to the tapered sidewalls 298, 300. In any embodiments, the distal tip portion 293 can provide greater flexibility to the distal tip 292 of the catheter 290, and can be added to any catheter embodiment disclosed herein.

Additionally, the distal tip portion 293 can have parallel, non-tapered top and bottom surfaces 312, 314 that have a different profile than the top and bottom surfaces 322, 324, which tapered top and bottom surfaces 322, 324 can be straight tapered, or have a curved tapered profile, or any other profile disclosed herein or desired. In any embodiments, the top and bottom surfaces 312, 314 of the distal end portion 293 of the distal tip 292 can be straight so as to have no change in thickness T along the length of the distal tip portion 293, or can be tapered and have the same taper as the tapered top and bottom surfaces 322, 324, or have a different taper as compared to the tapered top and bottom surfaces 322, 324.

As mentioned, any of the features, shapes, profiles, or other details of any of the embodiments disclosed herein can be substituted or used in combination with any of the other features, shapes, profiles, or other details of any of the other embodiments disclosed herein to form new embodiments. FIGS. 22A-22H show a variety of alternative cross-sectional profiles that can be applied to any of the catheter tip embodiments disclosed herein. The cross-sectional profiles are taken through a portion of the distal tip embodiments disclosed herein, for example, along line C-C in any one of FIGS. 17-20. As shown therein, any of the distal tip embodiments can have rectangular cross-sectional shape, an ovular cross-sectional shape, a diamond shaped cross-sectional shape, a diamond shaped cross-sectional shape with curved portions, the triangular-shaped, or a semicircular shaped, or any combination of the shapes along any portion of a length of the distal tip. Additionally, any of the embodiments can have channels, or ridges extending along all or a portion of the distal tip, symmetrically (on both sides of the section), or asymmetrically (one side only, or one side being greater than the opposite side).

Any of the asymmetrically shaped distal tip embodiments disclosed herein can permit the distal tip to have greater flexibility or bendability in one direction relative to the other. With any asymmetrically configured or shaped distal tips, the tip will be more flexible in one direction relative to the opposite direction. In any embodiments disclosed herein, rotating the catheter body can result in the direction of greater flexibility of the distal tip changing, to permit the catheter to adjust to changing directions of the vessels so that the asymmetric direction of the distal tip is pointed in the direction of the curvature. This will reduce the risk of perforation of the vessel wall.

The elliptical and diamond shaped sections provide can have lower friction than square cross-sections when advanced through the vasculature. An elliptical shape can be safer and cause less trauma on the vessel wall relative to a diamond shaped cross section.

Figure 23:
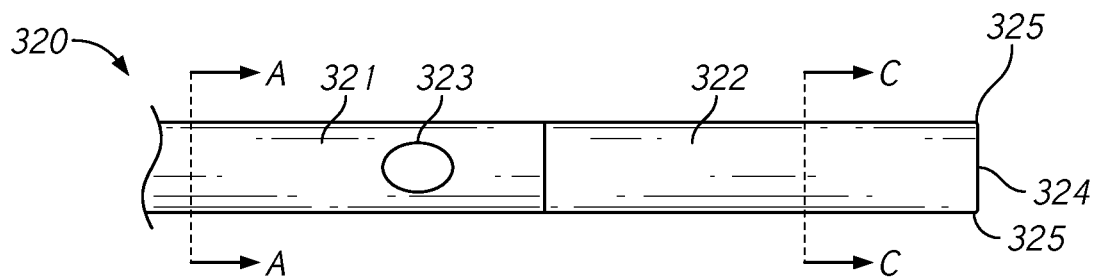
FIG. 23 is a top view of a distal portion of another catheter embodiment.

FIG. 23 is a top view of another embodiment of a reentry catheter 320 having catheter body 321, a distal tip 322, and a port 323 formed in the catheter body 321 and in communication with a lumen extending through the catheter body 321. The distal tip 322 can have a distal end 324 having a generally straight or square end portion 325. The end portion 325 can have rounded corners 325 to reduce trauma to the tissue, as shown. The distal end 324 can be used in place of a distal end of any other embodiments disclosed herein.

Figure 24:
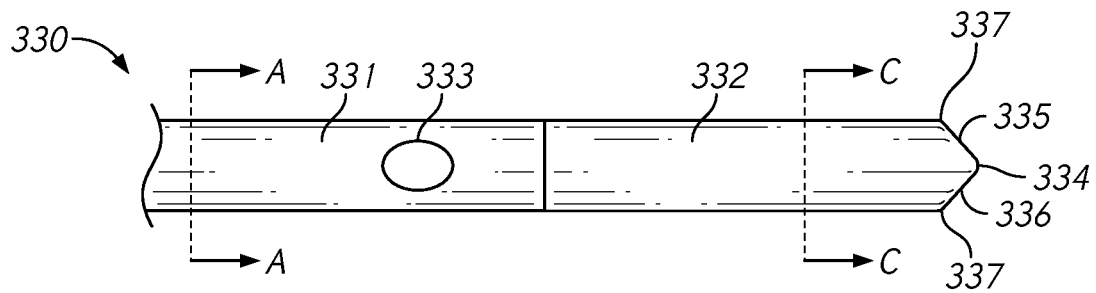
FIG. 24 is a top view of a distal portion of another catheter embodiment.

FIG. 24 is a top view of another embodiment of a reentry catheter 330 having catheter body 331, a distal tip 332, and a port 333 formed in the catheter body 331 and in communication with a lumen extending through the catheter body 331. The distal tip 332 can have a distal end 334 having a beveled shape. As shown, the distal end 334 can have a first angled surface 335 and a second angled surface 336. The first and second angled surfaces 335, 336 can be symmetric relative to one another about a centerline axis through the distal tip 332 of the catheter 330. The end portion of the distal tip 332 can have rounded corners 337 to reduce trauma to the tissue. The distal end 334 can be used in place of a distal end of any other embodiments disclosed herein.

Figure 25:
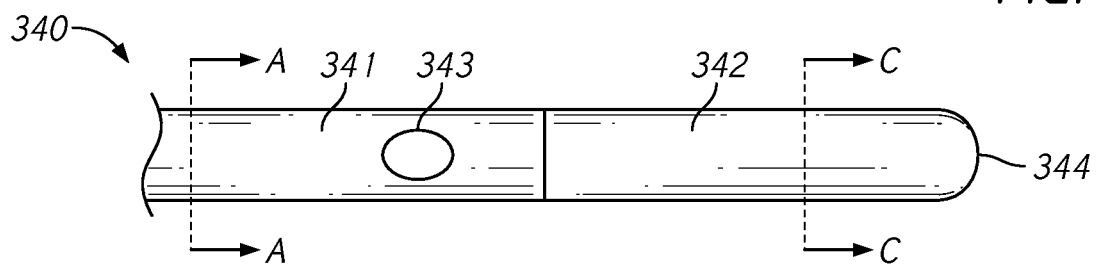
FIG. 25 is a top view of a distal portion of another catheter embodiment.

FIG. 25 is a top view of another embodiment of a reentry catheter 340 having catheter body 341, a distal tip 342, and a port 343 formed in the catheter body 341 and in communication with a lumen extending through the catheter body 341. The distal tip 342 can have a distal end 344 having a rounded or arcuate shape. As shown, the distal end 344 can have a distal end 344 that is circular, having a diameter that is approximately the same as a diameter of the catheter body 341. The distal end 344 can be used in place of a distal end of any other embodiments disclosed herein.

Figure 26:
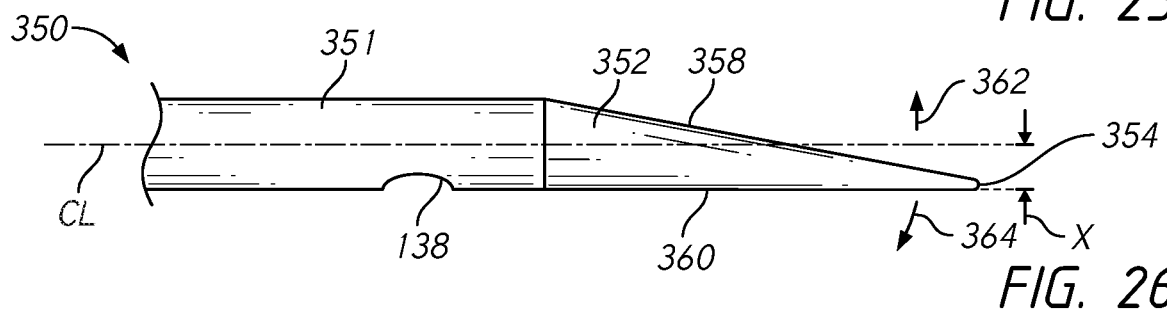
FIG. 26 is a side view of a distal portion of another catheter embodiment.

FIG. 26 is a side view of another embodiment of a reentry catheter 350 having catheter body 351 and a distal tip 352. As shown in FIG. 26, the distal tip 352 can have an asymmetric profile in a vertical direction about centerline axis CL. In this configuration, when the distal tip 352 is in a relaxed state (i.e., there are no external forces acting on the distal tip, except ambient forces by gravity) the distal end 354 of the distal tip 352 can be offset from the centerline axis CL of the catheter in the illustrated embodiment, the distal tip 354 and/or other portions of the distal tip 352 can be offset below the centerline axis CL. In this embodiment, a first (or top) surface 358 of the distal tip 352 can be tapered or angled to a greater extent than a second (or bottom) surface 360 of the distal tip 352. Additionally, in any embodiments, the bottom surface 360 of the distal tip 352 can be straight and not have any taper in it. In this configuration, the flexibility of the distal tip 354 can be different in one vertical direction as compared to the second, opposing vertical direction. For example, in the illustrated embodiment, the distal tip 352 can be less flexible in a first vertical direction 362 (which is toward the first surface 358) than in a second, opposing vertical direction 364.

In any embodiments, the distal end 354 of the distal tip 352 can deviate from the centerline CL of the catheter body by approximately 10% of the diameter of the catheter body 351, or from approximately 10% to approximately 100% or more of the diameter of the catheter body, or from approximately 20% to approximately 50% of the diameter of the catheter body. By 10% deviation, it is meant that a distance from the centerline CL of the catheter body 351 to a center of the distal end 354 of the distal tip 352 is approximately 10% of the diameter of the catheter body 351. For example, for a 5 Fr catheter having a diameter of approximately 0.066 inches and having a 50% deviation, a distance from the centerline CL of the catheter body 351 to a center of the distal end 354 of the distal tip 352 will be approximately 0.033 in.

Additionally, in this configuration, also, the distal port 138 can be positioned closest to the second surface 360 of the distal tip 352 so that the opening or port 138 points generally in the same radial direction as the second surface 360 of the distal tip 352. Alternatively, one or more the distal ports 138 can be positioned closest to the first surface 358 of the distal tip 352 so that the opening or port 138 points generally in the same radial direction as the first surface 358 of the distal tip 352.

Figure 27:
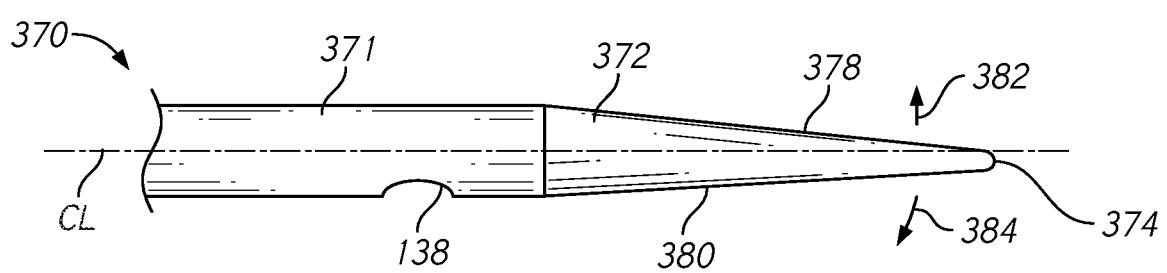
FIG. 27 is a side view of a distal portion of another catheter embodiment.

FIG. 27 is a side view of another embodiment of a reentry catheter 370 having a distal tip 372. As shown in FIG. 27, the distal tip 372 can have an asymmetric profile in a vertical direction about centerline axis CL, similar to the embodiment of the catheter 350 (which can be used for reentry procedures) described above. Any embodiments of the catheter 370 or components thereof disclosed herein can have any of the features, components, and/or other details of any of the other catheter embodiments or components thereof disclosed herein, including without limitation the embodiment of the catheter 350 described above. In some embodiments, the catheter 370 can have a less pronounced or less assymetric distal tip 372, wherein the deviation is less than the deviation of the embodiments of the catheter 350 described above.

FIG. 28A is an end view and 28B a side view of another embodiment of a reentry catheter 390 having catheter body 391 and a distal tip 392. The catheter 390 can have a port formed in the catheter body 391 and in communication with a lumen extending through the catheter body 391. The distal tip 392 can have a distal end 394 having a flat end that can be asymmetrically positioned in a vertical direction relative to a centerline extending through the axial center of the catheter when the distal tip 392 is in a relaxed state (for example, in a downward direction relative to the centerline, when viewed from the side). In any embodiments, the distal end 394 can be offset from the centerline extending through the axial center of the catheter by a distance X (not shown) that can be equal to approximately 15% of the diameter of the catheter body 391, or from approximately 10% to approximately 25%, or from approximately 10% to approximately 50% or more of the diameter of the catheter body 391, or to or from any values within these ranges. The amount or distance X of asymmetry can be the same as described for any other embodiments disclosed herein, including without limitation the values described for catheter 370.

In this configuration, the distal tip 392 can exhibit asymmetric flexibility in the upward and downward directions (i.e., in the up and down directions when viewed from the side of the catheter, as in FIG. 26). For example and without limitation, the distal tip 392 can have a flexibility in an upward direction that is less than a flexibility in the downward direction. In any embodiments, the catheter can be configured such that the flexibility in the upward direction is approximately 50% of the flexibility in the downward direction, or from approximately 20% or less to approximately 70% or more of the flexibility in the downward direction. The distal end 394 can have rounded edges 395 to reduce the trauma to any tissue. The distal tip 392 and distal end 394 can be used in place of the distal end of any other embodiments disclosed herein.

FIG. 29A is an end view and 29B a side view of another embodiment of a reentry catheter 410 having catheter body 411, a distal tip 412. The catheter 410 can have a port formed in the catheter body 411 and in communication with a lumen extending through the catheter body 411. The distal tip 412 can have a distal end 414 having a generally conical end that can be asymmetrically positioned relative to a centerline extending through the axial center of the catheter (for example, in a downward direction relative to the centerline, when viewed from the side). In any embodiments, the distal end 414 can be offset from the centerline extending through the axial center of the catheter by approximately 15% of the diameter of the catheter body 411, or from approximately 10% to approximately 25% or more of the diameter of the catheter body 411. The amount or distance of asymmetry can be the same as or similar to the amount or distance of asymmetry described for any other embodiments disclosed herein, including without limitation the values described for catheter 370. The distal end 414 can have rounded edges 415 to reduce the trauma to any tissue. The distal tip 412 and distal end 414 can be used in place of the distal end of any other embodiments disclosed herein.

FIG. 30 is a side view of another embodiment of a reentry catheter 500 having catheter body 501, a distal tip 502 have a distal end 504, and a port 510 formed through the catheter body 501. As with any of the catheter embodiments disclosed herein, alternatively, the port 510 can be formed in the distal tip 502. The port 510 can be in communication with an internal lumen extending along a length of the catheter body 501. The embodiment of the catheter 500 can have any of the other features, components, or other details of any of the other catheter embodiments disclosed herein, in combination with or in place of any of the features, components, or other details disclosed with respect to catheter 500 to form new embodiments. Similarly, any of the other catheter embodiments disclosed herein can have any of the features, components, or other details described herein with respect to catheter 500 in combination with or in place of any of the features, components, or other details disclosed with respect to the embodiment of the other catheter.

As shown in FIG. 30, the distal tip 502 can have a curved profile in a downward direction when viewed from the side as in FIG. 30. In particular, the catheter 500 can have a distal tip that bends or is curved in the downward direction relative to the axial centerline CL of the catheter 500 such that, in a relaxed state, a distal end 504 can be positioned below the axial centerline CL by a distance X from the centerline CL. This downward curvature also results in the distal tip 502 having an asymmetric profile in a vertical direction about centerline axis CL.

In any embodiments, when the distal tip 502 is in a relaxed state (i.e., there are no external forces acting on the distal tip, except ambient forces by gravity), the distal end 504 and/or a portion of the distal tip 502 can be offset below the centerline axis CL by a distance X. In this configuration, the flexibility of the distal tip 504 can be different in one vertical direction as compared to the second, opposing vertical direction. For example, in the illustrated embodiment, the distal tip 502 can be less flexible in a first vertical direction 516 (which is in the upward direction in FIG. 30) than in a second, opposing downward direction 518. One or more radiopaque markers can be added to the catheter body or distal tip to facilitate a surgeon in determining an orientation of the distal tip so that the surgeon can rotate the distal tip in the optimal orientation to navigate tortuous vasculature or otherwise.

In any embodiments, the distal end 504 of the distal tip 502 can deviate from the centerline CL of the catheter body by approximately 10% of the diameter of the catheter body 501, or from approximately 10% to approximately 100% or more of the diameter of the catheter body, or from approximately 20% to approximately 50% of the diameter of the catheter body. By 10% deviation, it is meant that a distance from the centerline CL of the catheter body 501 to a center of the distal end 504 of the distal tip 502 (represented by X in FIG. 30) is approximately 10% of the diameter of the catheter body 501. For example, for a 5 Fr catheter having a diameter of approximately 0.066 inches and having a 50% deviation, a distance from the centerline CL of the catheter body 501 to a center of the distal end 504 of the distal tip 502 will be approximately 0.033 in.

Additionally, in this configuration, the distal port 510 can be radially positioned so as to be pointing in the same radial direction that the distal tip 502 deviates toward (for example, in the downward direction as shown in FIG. 30), so that the opening or port 510 points generally in the same radial direction as the distal end 504 of the distal tip 502. Alternatively, the catheter 500 can have one or more ports pointing in any desired direction.

In this configuration, when the distal tip 502 is in a relaxed state (i.e., there are no external forces acting on the distal tip, except ambient forces by gravity) the distal end 504 of the distal tip 502 can be offset from the centerline axis CL of the catheter by a distance X. In the illustrated embodiment, the distal end 504 can be offset below the centerline axis CL by distance X. For example and without limitation, the distal tip 502 can have a flexibility 516 in an upward direction that is less than a flexibility 518 in the downward direction. In any embodiments, the catheter can be configured such that the flexibility 516 in the upward direction is approximately 50% of the flexibility 518 in the downward direction, or from approximately 20% or less to approximately 70% or more of the flexibility 518 in the downward direction.

Additionally, as with any of the embodiments disclosed herein that have asymmetric distal tips, the distal tip 502 can be curved away from the centerline CL at any desired angle (represented by A in FIG. 30). For example and without limitation, the distal tip 502 can be curved away from the centerline CL at any desired angle. For example, in any embodiments, the distal tip 502 can be curved away from the centerline CL at an approximately 35 degree angle, or from approximately 20 degrees to approximately 50 degrees, or from approximately 10 degrees to approximately 70 degrees.

FIG. 31A illustrates a catheter having a straight (but tapered) catheter tip and FIG. 31B a catheter having a curved tip being advanced through a vessel lumen. As illustrated in FIG. 31B, the curved tipped catheter can follow the vessel wall in a curved section of the vessel wall with a lower likelihood of perforating the vessel wall and/or causing less trauma to the vessel wall.

Figure 32:
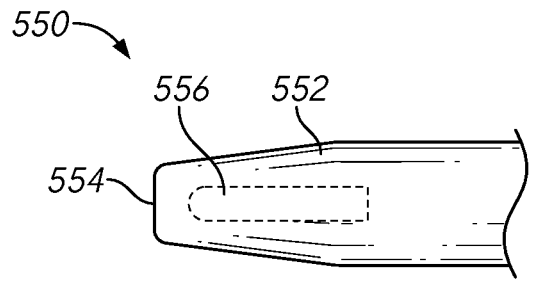
FIG. 32 is a top view of a distal portion of another catheter embodiment.
Figure 33:
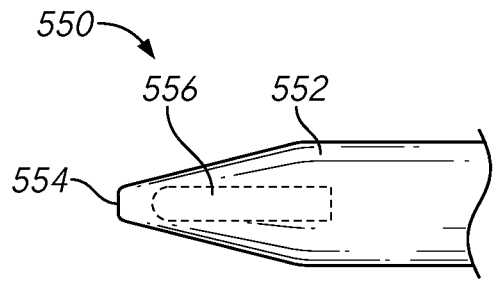
FIG. 33 is a side view of the distal portion of the catheter embodiment shown in FIG. 32.
Figure 34:
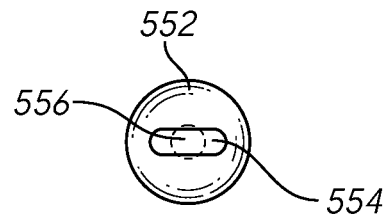
FIG. 34 is an end view of the distal portion of the catheter embodiment shown in FIG. 32.

FIGS. 32, 33, and 34 are a top view, side view, and front end view, respectively, of another embodiment of a catheter 550 having a distal tip 552 and a distal end 554. The embodiment of the catheter 550 can have any of the features, components, or other details of any of the other catheter embodiments disclosed herein, in combination with or in place of any of the features, components, or other details disclosed with respect to catheter 550 to form new embodiments. Similarly, any of the other catheter embodiments disclosed herein can have any of the features, components, or other details described herein with respect to catheter 550 in combination with or in place of any of the features, components, or other details disclosed with respect to the embodiment of the other catheter. With reference to FIGS. 32-34, the distal tip 552 of the catheter 550 can have a core member 556 therein configured to increase a bending stiffness of the distal tip 552. The core member 556 can be comprise any desired material or mix of materials, including without limitation nickel titanium (Nitinol), stainless steel, polymer material, or any other shape memory materials or suitable materials. In any embodiments, the core member 556 can increase the durability of the distal tip.

In the illustrated embodiment, the distal end 554 has a generally flat shape, but the distal tip 552 is generally tapered on the side walls. The core member 556 can be symmetrically shaped in all directions about a centerline axis, or can be asymmetric so as to be more flexible in a vertical direction (for example, up or down in the side view shown in FIG. 33). Additionally, in any embodiments, the core member 556 can be configured to be more flexible in one direction relative to the opposite direction. In the illustrated embodiment, the core member has a generally symmetric cross-sectional shape and a rounded distal end portion. The core member 556 can have a diameter of approximately 0.002 in (0.05 mm) to approximately half of the diameter of the catheter shaft. In any embodiments, the core member 556 can be tapered in one or both of the vertical and lateral directions.

Figure 35:
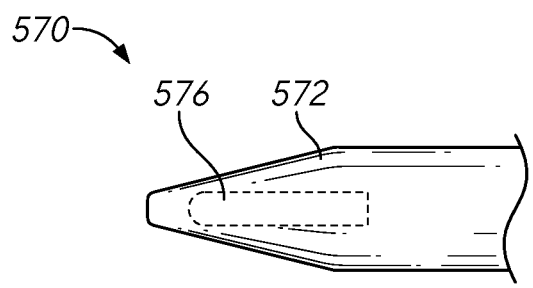
FIG. 35 is a top view of a distal portion of another catheter embodiment.
Figure 36:
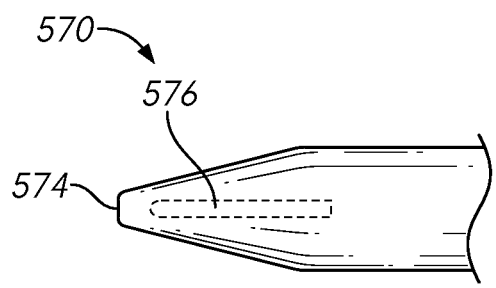
FIG. 36 is a side view of the distal portion of the catheter embodiment shown in FIG. 35.
Figure 37:
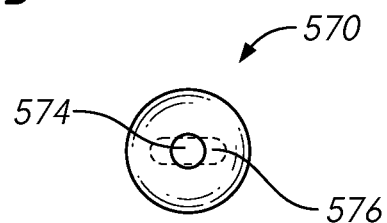
FIG. 37 is an end view of the distal portion of the catheter embodiment shown in FIG. 35.
Figure 45A:
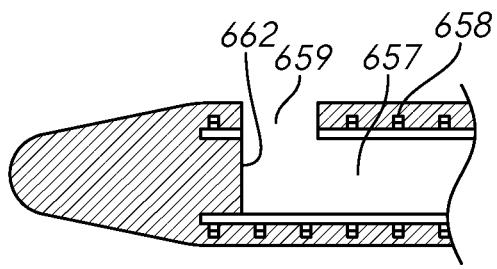
FIG. 45A is a section view of a distal portion of another catheter embodiment.
Figure 45B:
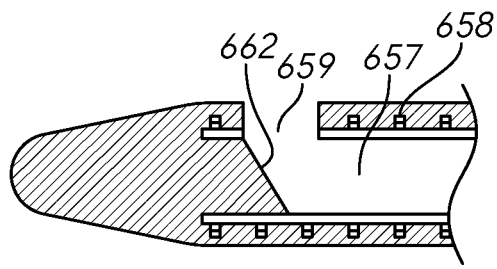
FIG. 45B is a section view of a distal portion of another catheter embodiment.
Figure 45C:
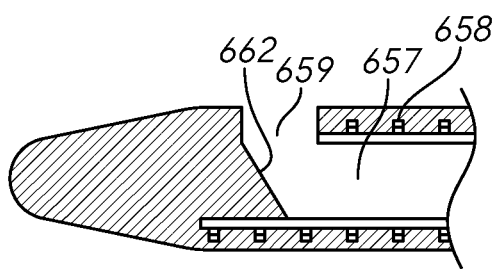
FIG. 45C is a section view of a distal portion of another catheter embodiment.
Figure 45D:
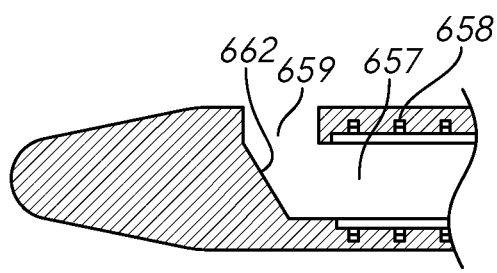
FIG. 45D is a section view of a distal portion of another catheter embodiment.
Figure 45E:
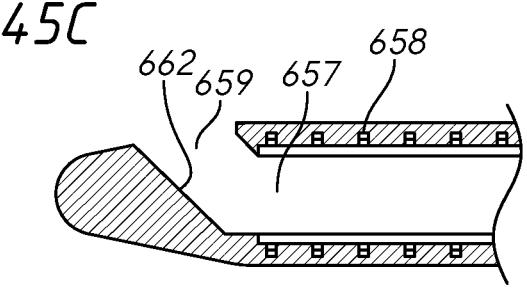
FIG. 45E is a section view of a distal portion of another catheter embodiment.

FIGS. 35, 36, and 37 are a top view, side view, and front end view, respectively, of another embodiment of a catheter 570 having a distal tip 572 and a distal end 574. The embodiment of the catheter 570 can have any of the features, components, or other details of any of the other catheter embodiments disclosed herein, in combination with or in place of any of the features, components, or other details disclosed with respect to catheter 570 to form new embodiments. Similarly, any of the other catheter embodiments disclosed herein can have any of the features, components, or other details described herein with respect to catheter 570 in combination with or in place of any of the features, components, or other details disclosed with respect to the embodiment of the other catheter. With reference to FIGS. 35-37, the distal tip 572 of the catheter 570 can have a core member 576 therein configured to increase a bending stiffness of the distal tip 572. The core member 576 can be comprise any desired material or mix of materials, including without limitation nickel titanium (Nitinol), stainless steel, polymer material, or any other shape memory materials or suitable materials.

In the illustrated embodiment, the distal end 574 has a round flat shape, and the distal tip 574 is generally conically tapered. The core member 576 can be asymmetric (for example, having a greater width—as shown in FIG. 35—than a height—for example, as shown in FIG. 36) so as to be more flexible in a vertical direction (for example, up or down in the side view shown in FIG. 36) than in a lateral direction. Additionally, in any embodiments, the core member 576 can be configured to be more flexible in one direction relative to the opposite direction. In the illustrated embodiment, the core member 576 has a generally symmetric cross-sectional shape and a rounded distal end portion.

FIGS. 38 and 39 are a side view and a section view taken through line 39-39, respectively, of another embodiment of a catheter 600 having a distal tip 602 and a distal end 604. The embodiment of the catheter 600 can have any of the features, components, or other details of any of the other catheter embodiments disclosed herein, in combination with or in place of any of the features, components, or other details disclosed with respect to catheter 600 to form new embodiments. Similarly, any of the other catheter embodiments disclosed herein can have any of the features, components, or other details described herein with respect to catheter 600 in combination with or in place of any of the features, components, or other details disclosed with respect to the embodiment of the other catheter. The distal tip 602 of the catheter 600 can have a core member 606 therein configured to increase a bending stiffness of the distal tip 602. The core member 606 can be comprise any desired material or mix of materials, including without limitation nickel titanium (Nitinol), stainless steel, polymer material, or any other shape memory materials or suitable materials.

The core member 606 can be asymmetric, for example, having a greater width (as shown in FIG. 39), than a height so as to be more flexible in a vertical direction than in a lateral direction. In any embodiments, the core member 606 can have a generally rectangular cross-sectional shape, having a width that is greater than a height. In any embodiments, the width can be approximate three times greater than the height, or from approximately two times greater to approximately four or more times greater than the height. Additionally, in any embodiments, the core member 606 can be configured to be more flexible in one direction relative to the opposite direction. In the illustrated embodiment, the core member 606 has a generally symmetric cross-sectional shape.

FIGS. 40, 41, and 42 are a side view, a first section view, and a second section view taken through line 41-41, respectively, of another embodiment of a catheter 610 having a distal tip 612 and a distal end 614. The embodiment of the catheter 610 can have any of the features, components, or other details of any of the other catheter embodiments disclosed herein, in combination with or in place of any of the features, components, or other details disclosed with respect to catheter 610 to form new embodiments. Similarly, any of the other catheter embodiments disclosed herein can have any of the features, components, or other details described herein with respect to catheter 610 in combination with or in place of any of the features, components, or other details disclosed with respect to the embodiment of the other catheter. The distal tip 612 of the catheter 610 can have a core member 616 therein configured to increase a bending stiffness of the distal tip 612. The core member 616 can be comprise any desired material or mix of materials, including without limitation nickel titanium (Nitinol), stainless steel, polymer material, or any other shape memory materials or suitable materials.

The core member 616 can be asymmetric, for example, having a greater width (as shown in FIG. 41), than a height so as to be more flexible in a vertical direction than in a lateral direction. Alternatively, the core member 616 can have a round cross-sectional shape, as shown in FIG. 42. In any embodiments, the width can be approximate two times greater than the height, or from approximately two times greater to approximately four or more times greater than the height. Additionally, in any embodiments, the core member 616 can be configured to be more flexible in one direction relative to the opposite direction. In the illustrated embodiment, the core member 616 has a generally symmetric cross-sectional shape.

FIG. 43 is a side view of another embodiment of a catheter 630 having a catheter body 631, a distal tip 632, a lumen 634 extending through at least a portion of the catheter body 631, and a port 635 at a distal end of the lumen 634. The embodiment of the catheter 630 can have any of the features, components, or other details of any of the other catheter embodiments disclosed herein, in combination with or in place of any of the features, components, or other details disclosed with respect to catheter 630 to form new embodiments. Similarly, any of the other catheter embodiments disclosed herein can have any of the features, components, or other details described herein with respect to catheter 630 in combination with or in place of any of the features, components, or other details disclosed with respect to the embodiment of the other catheter.

With reference to FIG. 43, the port 635 can be positioned in the catheter body 631 before the proximal end 636 of the distal tip 632. The port 635 can be formed at any desired angle relative to the centerline CL of the catheter body 631. For example, the port 635 can extend away from the centerline CL of the catheter body 631 at an angle A relative to the centerline CL. In any embodiments, the angle A can be approximately 45 degrees, or from approximately 30 degrees to approximately 90 degrees or more relative to the centerline CL. Providing an angle A that is less than approximately 60 degrees can permit a guidewire being advanced through the lumen 634 to more easily advance through the port 635 without binding or being impeded by a sharp angle adjacent to the port 635. FIG. 44 is side view of another embodiment of a catheter 650 wherein the port 655 is formed through or exits through the distal tip 652 of the catheter 650. The embodiment of the catheter 650 can be similar to the embodiment 630 in all other regards.

FIGS. 45A-45E are section views of distal end portions of additional catheter embodiments. Each of the embodiments illustrated in FIGS. 45A-45E has a lumen 657 extending through the catheter body and a portion of the distal tip, a reinforcing braid or coil arrangements 658 (though not required) that can extend at least as far as or even farther than the lumen 657, and at least one distal port 659 that can be positioned in any of a range of different locations. Any of the embodiments can also have a ramp or angled end portion 662 positioned at a distal end of the lumen that can be configured to direct or bias a guidewire advancing through the lumen 657 toward the distal port 659 and out of the catheter body in a direction that is generally lateral to a longitudinal centerline of the catheter bodies.

Figure 46A:
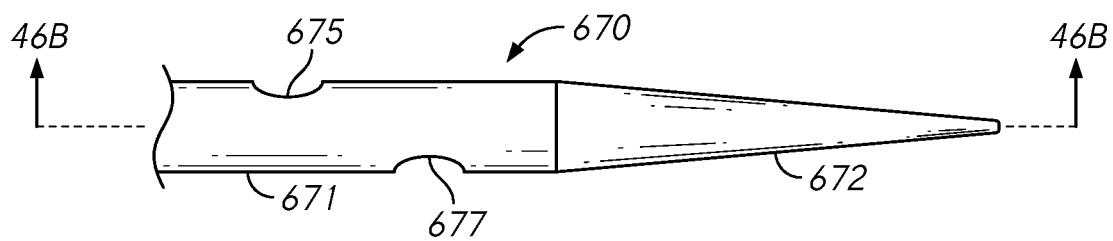
FIG. 46A is a side view of a distal portion of another catheter embodiment.
Figure 46B:
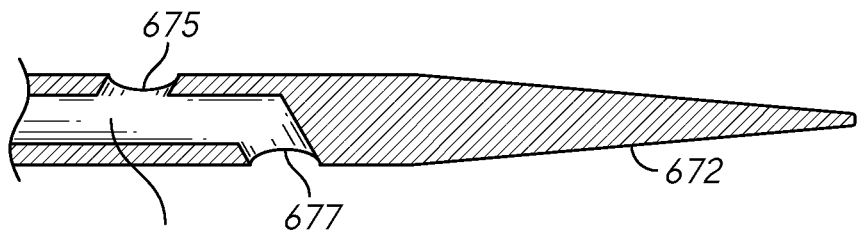
FIG. 46B is a section view of the catheter embodiment shown in FIG. 46A.

FIG. 46A is a side view of another embodiment of a catheter 670 having a catheter body 671, a distal tip 672, a first port 675, and a second port 677. The first and second ports 675, 677 can be formed in any desired position on the catheter body 671 and/or distal tip 672. The first and second ports 675, 677 can be formed in generally mutually opposing directions, so that a guidewire exiting from the first port 675 is advanced away from the lumen in a first direction that is generally in the opposite radial direction than a guidewire exiting from the second port 677 (noting though that, since the ports are not formed at 90 degrees relative to the lumen, the ports will not be in 180 degree opposing directions). FIG. 46B is a section view of the embodiment of the catheter 670, showing one arrangement of how the first and second ports 675, 677 can be formed in communication with a lumen 679 extending through the catheter body 671.

Figure 47:
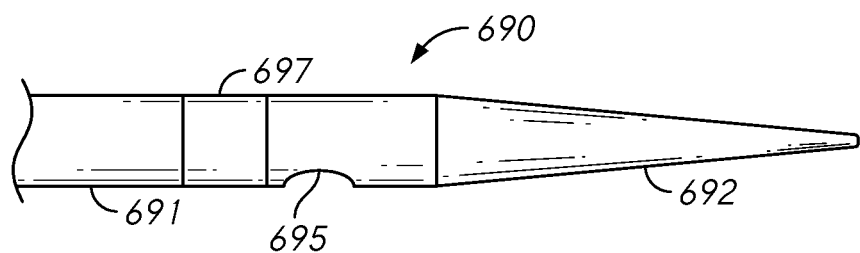
FIG. 47 is a side view of a distal portion of another catheter embodiment.

FIG. 47 is a side view of another embodiment of a catheter 690 having a catheter body 691, a distal tip 692, a port 695, and a radiopaque marker 697. The radiopaque marker 697 can be a band of radiopaque material, and can be positioned adjacent to the port 695, either proximal (as shown), distal to, or generally aligned with the port 695. Any embodiments disclosed herein can have two or more radiopaque markers or bands positioned at any desired location on the catheter. Any of the radiopaque markers can comprise barium, platinum, tungsten, or any other desired radiopaque material or combination thereof. Additionally, in any embodiments, the radiopaque band(s) and/or marker(s) can be positioned so that a surgeon can determine the radial orientation and/or the location of the catheter body, the catheter tip, and/or the ports when viewed under fluoroscopy. For example, a first radiopaque marker can be positioned adjacent to the port along one side of the catheter body, or surrounding the port, so that a surgeon can determine the location of the port and the radial orientation of the catheter relative to the patient's vasculature.

Additionally, in any embodiments, a second radiopaque marker can be positioned on a radially opposite side of the catheter body and at a distance in the proximal direction or distal direction (whichever is desired) relative to the first radiopaque marker such that the surgeon can determine when the catheter is in a particular orientation (with the two markers are spaced the furthers apart in the lateral direction (as opposed to being aligned with the centerline of the catheter, in which case the catheter would be rotated at a 90 degree angle). The further radiopaque marker can be used to indicate the side of the catheter that should be positioned closest to the vessel wall. For example, the catheter could have an asymmetrical tip that is more flexible in the direction away from the distal most marker. Other configurations are possible.

Figure 48:
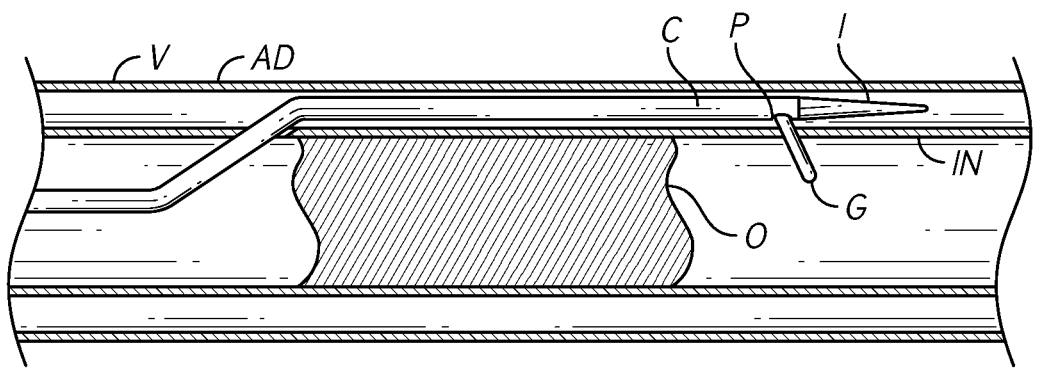
FIG. 48 is a section schematic view of an embodiment of a reentry catheter bypassing an occlusion

With reference to FIG. 48, the blood vessel is represented by V, the adventitia layer is represented by AD, the occlusion is represented by O, the intermediate layer is represented by I, and the intimal layer is represented by IN. In general, any catheter embodiments disclosed herein can be configured to be used for the following steps (in any desired order. The catheter C can be used to bypass the occlusion O through the sub-intimal or intermediate space I in the vessel V, and can be advanced such that the port P is positioned distal to the occlusion O. The catheter C can be oriented so that the distal port P is facing in the direction of the inside of the lumen. Radiopaque markers can be used to verify the orientation of the port and catheter body. The surgeon or medical practitioner can advance a guidewire through the lumen in the catheter body and through the port. The guidewire G can inwardly penetrate the intimal layer IN of the vessel wall and advance into the true lumen of the vessel. The guidewire G can therefore bypass the occlusion O, with the distal end of the guidewire being positioned within the lumen. Maintaining the approximate position of the guidewire, the catheter can be withdrawn, leaving the guidewire in place. The guidewire can then be used to direct other therapeutic devices to treat the affected area.

Figure 49A:
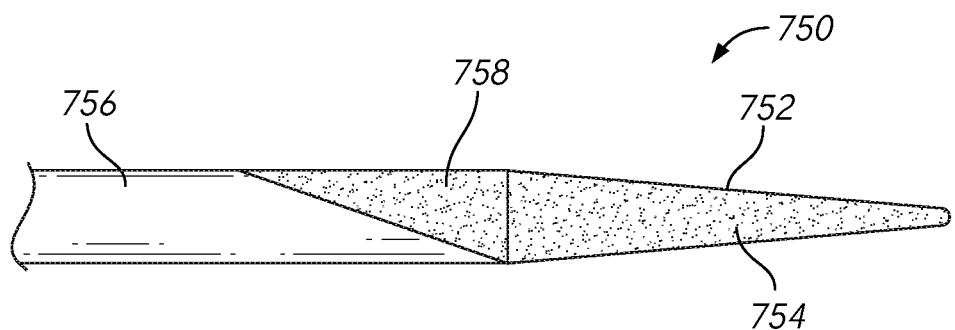
FIG. 49A is a side view of a distal portion of another catheter embodiment.

FIG. 49A is a side view of a distal portion of another catheter embodiment 750 having a distal tip coated with or comprising a radiopaque material, and a catheter body 756 that has a radiopaque portion 758 adjacent to the distal tip region. One or both of the radiopaque regions or portions 754, 758 can be used to identify the location of the distal end portion of the catheter to the surgeon or user and/or assist the surgeon or user in identifying the orientation of the catheter body to determine the direction that the distal port is facing. In any embodiments, such as the embodiment of the catheter 750 shown in FIG. 49A, the radiopaque portion 758 adjacent to the distal tip 752 can have an angled or tapered shape, which can assist the surgeon in identifying the orientation of the catheter body and, hence, location of the distal port. Any catheter embodiments disclosed herein can have a radiopaque portion 758 having a length from approximately 0.04 in (1 mm) to approximately 0.47 in (12 mm), or from approximately 0.12 in (3 mm) to approximately 0.35 in (9 mm).

Figure 49B:
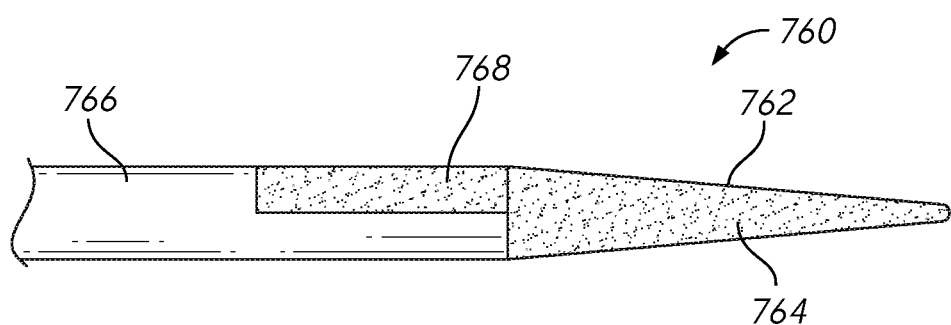
FIG. 49B is a side view of a distal portion of another catheter embodiment.

FIG. 49B is a side view of a distal portion of another catheter embodiment 760 having a distal tip coated with or comprising a radiopaque material, and a catheter body 766 that has a radiopaque portion 768 adjacent to the distal tip region. One or both of the radiopaque regions or portions 764, 768 can be used to identify the location of the distal end portion of the catheter to the surgeon or user and/or assist the surgeon or user in identifying the orientation of the catheter body to determine the direction that the distal port is facing. In any embodiments, such as the embodiment of the catheter 760 shown in FIG. 49B, the radiopaque portion 768 adjacent to the distal tip 762 can cover only half of the circumference of the catheter body, which can assist the surgeon in identifying the orientation of the catheter body and, hence, location of the distal port. Any catheter embodiments disclosed herein can have a radiopaque portion 768 having a length from approximately 0.04 in (1 mm) to approximately 0.47 in (12 mm), or from approximately 0.12 in (3 mm) to approximately 0.35 in (9 mm). Additionally, in any embodiments, a height of the radiopaque portion 768 can be approximately 50% of the height or diameter of the catheter body.

Any components of any embodiments disclosed herein can be made from any suitable materials. Such materials can include thermoplastic polymers, including but not limited to nylon, polyurethane, Pebax, HDPE, PE, polyolefin and the like, and/or metal alloys such as stainless steel, Nitinol, and others. Stainless steel metal wire can be used for reinforcement. The wire can be fabricated into a braid mesh or coil embedded within the polymer layer to provide stiffness, flexibility and kink resistance properties. Braid can use approximately 0.001 in, approximately 0.0015 in, or approximately 0.002 in wires formed into a mesh using a PICC count of 150 to 30. Alternatively, such wires can be formed into coils along any portion of the length of the catheter body, including at a distal section of the catheter body. Then, the wire coils can transition into wire braiding with or without an overlap of 1 to 0.079 in (2 mm) proximal to the distal end portion of the catheter body.

Any embodiments can have a distal tip, which can be made from a polyurethane or nylon with or without tungsten loaded resin. Tungsten loaded resin for the tip can be used to provide visual feedback to the user under x-ray of the location of the tip. The proximal shaft can use a Grilamid L25 to provide a stiff end for pushing. A middle section of the catheter body can transition to Pebax 72D, Pebax 70D, Pebax 63D, Pebax 55D and have Pebax 40D and 35D for the distal end soft section, which can comprise about 10-15 cm of the distal end. If the catheter is used for other areas such as lower limb vasculature, stiffer polymers instead of 40D or 35D Pebax can be used to achieve a stiffer distal end.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A reentry catheter comprising:
a catheter body having a first end and a second end;
a lumen extending axially through a length of the catheter body;
a distal port in communication with the lumen, the distal port being at an acute angle relative to an axial centerline of the catheter body; and
a flexible distal tip positioned at a distal end of the catheter body, the distal tip having a first planar surface and a second planar surface that are angled to form a tapered portion in the distal tip, wherein:
the first and second planar surfaces of the distal tip extend along a length of the tapered portion generally to a distal end of the distal tip such that the tapered portion of the distal tip extends to the distal end of the distal tip;
a thickness of the tapered portion in a first direction decreases along the length of the tapered portion and is less than a width of the tapered portion in a second direction at every point along the length of the tapered portion such that the tapered portion of the tip is more flexible when bent in the first direction than in the second direction, the second direction being normal to the first direction; and
the port is in communication with the lumen and is configured to direct a guidewire that is advanced through the lumen out of the port in a lateral direction, the lateral direction being in a plane that is coincident with the first direction of the tapered portion and intersects the axial centerline of the catheter body.

2. The reentry catheter of claim 1, wherein the distal end of the tapered portion is at least approximately two times as flexible in the first direction as compared to the second direction.

3. The reentry catheter of claim 1, wherein the distal end of the tapered portion is from approximately three times to approximately five times as flexible in the first direction as compared to the second direction.

4. The reentry catheter of claim 1, wherein the distal tip has an asymmetric shape such that the distal tip is more flexible in the first direction than in a third direction, wherein the third direction is opposite to the first direction.

5. The reentry catheter of claim 1, wherein the distal end portion of the distal tip is offset from a centerline of the distal tip by a distance that is from approximately 10% to approximately 50% of the diameter of the catheter body.

6. The reentry catheter of claim 1, wherein, at any point along the tapered portion of the distal tip, a second moment of area of the distal tip in the second direction is greater than a second moment of area of the distal tip in the first direction.

7. The reentry catheter of claim 1, wherein a second moment of area of the distal tip in the second direction is greater than a second moment of area of the distal tip in the first direction at all points along a length of the tapered portion and wherein a difference between the second moment of area of the distal tip in the second direction and the second moment of area of the distal tip in the first direction increases along the length of the tapered portion.

8. The reentry catheter of claim 1, further comprising a radiopaque marker adjacent to the distal port.

9. The reentry catheter of claim 1, further comprising a core member positioned in the tapered portion configured to increase a bending stiffness of the distal tip in the second direction more than in the first direction.

10. The reentry catheter of claim 1, wherein the port is configured to direct a guidewire that is advanced through the lumen out of the port at an angle of from approximately 35 degrees to approximately 90 degrees relative to the axial centerline of the catheter body.

11. The reentry catheter of claim 1, wherein the width of the tapered portion of the distal tip continually decreases along the length of the tapered portion.

12. The reentry catheter of claim 1, wherein the catheter body comprises one or more of single wire braiding, multi-wire braiding, coils, and any other suitable metal support structures.

13. A reentry catheter comprising:
    a catheter body having a first end and a second end;
    a lumen extending axially through a length of the catheter body;
    a distal port in communication with the lumen, the distal port extending generally in a first direction away from an axial centerline of the catheter body; and
    a flexible distal tip positioned at a distal end of the catheter body, a distal end portion of the distal tip having:
        a first stiffness when a distal end portion of the distal tip is bent in the first direction; and
        a second stiffness when the distal end portion of the distal tip is bent in a second direction that is normal to the first direction;
    wherein:
        the second stiffness of the distal tip when the distal tip is bent in the second direction is greater than the first stiffness of the distal tip when the distal tip is bent in the first direction at every point along a length of the distal tip; and
        the first stiffness of the distal tip when the distal end portion of the distal tip is bent in the first direction decreases along the length of the distal tip such that the first stiffness is lowest at the distal end of the distal tip.

14. The reentry catheter of claim 13, wherein the second stiffness of the distal end portion of the distal tip when the distal end portion of the distal tip is bent in the second direction is at least approximately twice as high as the first stiffness of the distal end portion of the distal tip when the distal end portion of the distal tip is bent in the first direction.

15. The reentry catheter of claim 13, wherein the second stiffness of the distal end portion of the distal tip when the distal end portion of the distal tip is bent in the second direction is at least approximately three times as high as the first stiffness of the distal end portion of the distal tip when the distal end portion of the distal tip is bent in the first direction.

16. The reentry catheter of claim 13, wherein a width of the distal tip is approximately the same as or less than a width of the catheter body.

17. The reentry catheter of claim 13, wherein the port is configured to direct a guidewire that is advanced through the port to an angle that is from approximately 35 degrees to approximately 90 degrees relative to the axial centerline of the catheter body.

18. The reentry catheter of claim 13, further comprising a radiopaque marker adjacent to the distal port.

19. The reentry catheter of claim 13, further comprising a core member positioned in the distal tip configured to increase a bending stiffness of the distal tip in the second direction more than in the first direction.

20. The reentry catheter of claim 13, wherein the catheter body comprises one or more of single wire braiding, multi-wire braiding, coils, and any other suitable metal support structures.

21. The reentry catheter of claim 13, further comprising a means for identifying an orientation of the distal tip in fluoroscopy.

22. The reentry catheter of claim 13, further comprising a means for reducing the first stiffness of the distal tip in the first direction.

23. The reentry catheter of claim 13, further comprising a means for deflecting a guidewire through the distal port.

* * * * *